(12) United States Patent
Lee et al.

(10) Patent No.: US 10,033,307 B2
(45) Date of Patent: Jul. 24, 2018

(54) SAMPLE LOADING DEVICE FOR ELECTROSTATIC LEVITATION APPARATUS

(71) Applicant: Korea Research Institute of Standards and Science, Daejeon (KR)

(72) Inventors: Geun-Woo Lee, Daejeon (KR); Sangho Jeon, Daejeon (KR); Dong-Hee Kang, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 511 days.

(21) Appl. No.: 14/840,525

(22) Filed: Aug. 31, 2015

(65) Prior Publication Data
US 2016/0028330 A1    Jan. 28, 2016

Related U.S. Application Data

(63) Continuation of application No. PCT/KR2014/001929, filed on Mar. 10, 2014.

(30) Foreign Application Priority Data

Mar. 13, 2013    (KR) .................. 10-2013-0026525
Mar. 13, 2013    (KR) .................. 10-2013-0026531

(51) Int. Cl.
*H02N 13/00*    (2006.01)
*G01N 1/28*    (2006.01)
(Continued)

(52) U.S. Cl.
CPC ............. *H02N 13/00* (2013.01); *F27B 17/02* (2013.01); *G01N 1/28* (2013.01); *G01N 11/00* (2013.01)

(58) Field of Classification Search
CPC .......... H02N 13/00; F27B 17/02; G01N 1/28; G01N 11/00
(Continued)

(56) References Cited

U.S. PATENT DOCUMENTS 7,200,493 B2    4/2007  Nilsson et al.
7,447,250 B2   11/2008  Kawasaki et al.
(Continued)

FOREIGN PATENT DOCUMENTS

JP    2007-008769 U    2/1995
JP      2599320 Y2    9/1999
(Continued)

OTHER PUBLICATIONS

IPRP with Written Opinion for Application No. PCT/KR2014/001929 dated Sep. 15, 2015.
(Continued)

*Primary Examiner* — Kevin J Comber
(74) *Attorney, Agent, or Firm* — Jenkins, Wilson, Taylor & Hunt, P.A.

(57) ABSTRACT

Sample loading device and electrostatic levitation apparatus. The electrostatic levitation apparatus includes a sample storage part including a rod-shaped sample standby part having an external diameter of a first diameter and a rod-shaped sample loading part having an external diameter of a second diameter and a sample cover part covering the sample standby part. The sample storage part has a loading bar inserting hole formed in its center. The loading bar inserting hole is formed through the sample standby part and is formed successively through a portion of the sample loading part. The sample standby part has sample storage vertical through-holes. The sample loading part has a single sample transfer vertical through-hole. The sample transfer vertical through-hole is formed on a surface where the sample storage vertical through-hole is viewed, penetrates the sample loading part, and is connected to the loading bar inserting hole.

11 Claims, 15 Drawing Sheets

(51) Int. Cl.
*F27B 17/02* (2006.01)
*G01N 11/00* (2006.01)
(58) Field of Classification Search
USPC .......................................................... 361/233
See application file for complete search history.

(56) References Cited

U.S. PATENT DOCUMENTS

2005/0024808 A1* 2/2005 Kawasaki ............... F27B 17/00
361/234
2010/0274237 A1 10/2010 Yamakawa et al.

FOREIGN PATENT DOCUMENTS

| | | |
|---|---|---|
| JP | H11-241888 A | 9/1999 |
| JP | 2002-157592 A | 5/2002 |
| JP | 2003-075078 A | 3/2003 |
| JP | 2004-286298 A | 10/2004 |
| JP | 4270368 B2 | 5/2009 |
| JP | 2011-241888 A | 12/2011 |
| JP | 4914544 B2 | 4/2012 |

OTHER PUBLICATIONS

Park, CheolMin, "Density, viscosity, and surface tension measurement of metallic liquids at high temperature using an electrostatic levitation," University of Science & Technology, Master's Thesis (Notice on Electronic Library Jan. 2013) pp. 24-31.
International Search Report for Application No. PCT/KR 2014/001929 dated Jun. 16, 2014.

* cited by examiner

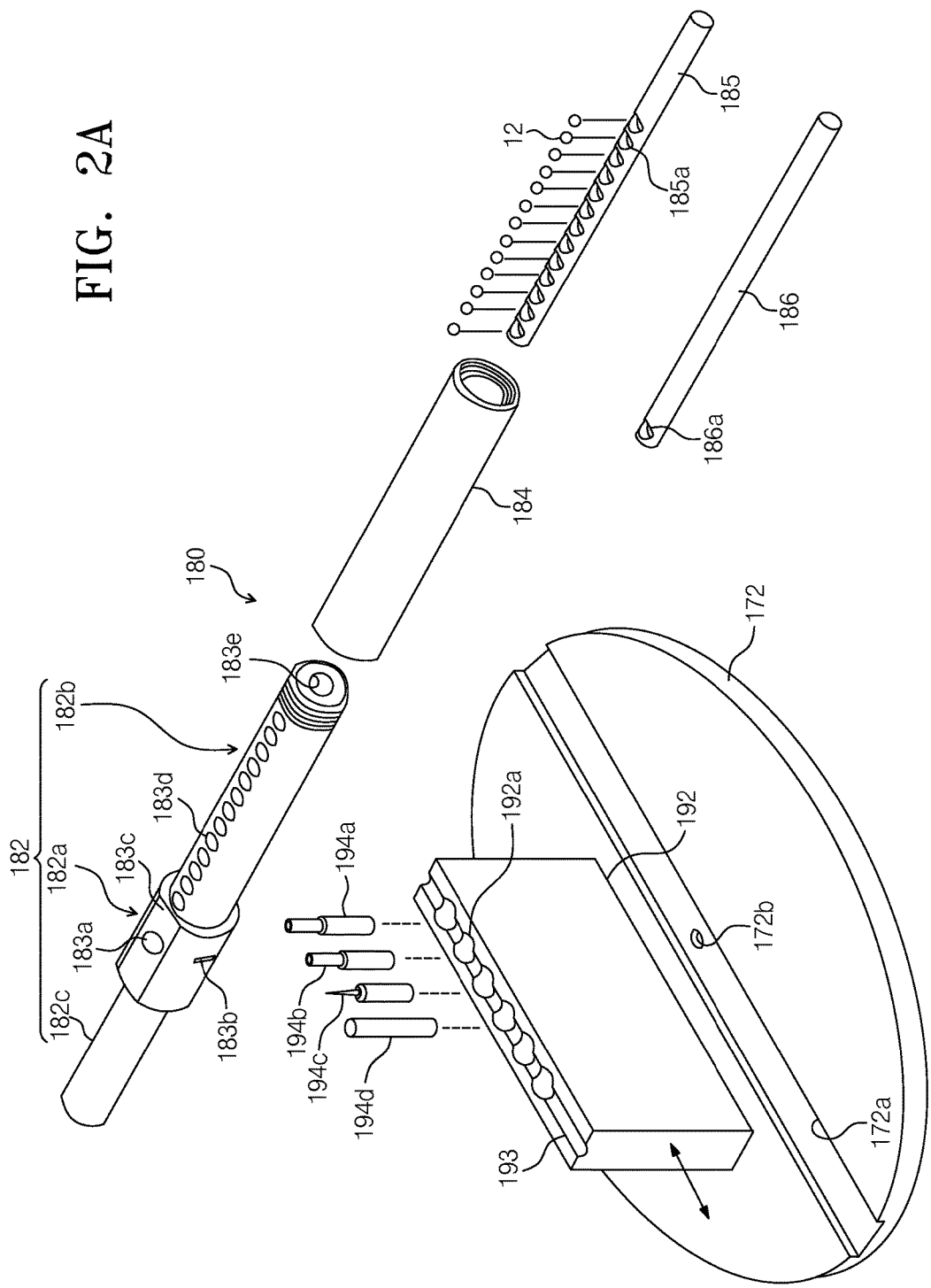

SAMPLE LOADING DEVICE FOR ELECTROSTATIC LEVITATION APPARATUS

CROSS-REFERENCE TO RELATED APPLICATIONS

This application is a continuation of and claims priority to PCT/KR2014/001929 filed on Mar. 10, 2014, which claims priority to Korea Patent Application No. 10-2013-0026525 filed on Mar. 13, 2013, Korea Patent Application No. 10-2013-0026531 filed on Mar. 13, 2013, the entireties of which are both hereby incorporated by reference.

BACKGROUND

1. Technical Field

The present disclosure generally relates to sample loading devices and, more particularly, to a sample loading device for use in an electrostatic levitation apparatus.

The present disclosure generally relates to electrostatic levitation apparatuses and, more particularly, to an electrostatic levitation apparatus with a loading tip storage.

2. Description of the Related Art

An electrostatic levitation apparatus may levitate charged samples. The electrostatic levitation apparatus may fuse levitated samples to be used in a material property study.

SUMMARY

Embodiments of the present disclosure provide a sample loading device which is capable of successively supplying samples.

Embodiments of the present disclosure provide an electrostatic levitation apparatus including a tip which is capable of performing various tests.

An example embodiment of the present disclosure provides a sample loading device. The sample loading device includes: a sample storage part including a cylindrical sample standby part having an external diameter of a first diameter and a cylindrical sample loading part having an external diameter of a second diameter; and a cylindrical sample cover part having an external diameter of the second diameter and covering the sample standby part. The sample storage part may have a loading bar inserting hole that is formed in its center in a lengthwise direction. The loading bar inserting hole may be formed through the sample standby part and may be formed successively through a portion of the sample loading part. The sample standby part may have sample storage vertical through-holes that are formed at regular intervals in a lengthwise direction and penetrate in a direction perpendicular to the lengthwise direction. The sample loading part may have single sample transfer vertical through-hole. The sample transfer vertical through-hole may be formed on a surface where the sample storage vertical through-hole is viewed, may penetrate the sample loading part, and may be connected to the loading bar inserting hole.

In an example embodiment, one surface to which the sample transfer vertical through-hole is exposed may be formed as a plane.

In an example embodiment, the sample loading device may further include a slit formed on both side surface of the sample loading part to be perpendicular to a direction in which the sample transfer vertical through-hole is formed. The slit may be connected to the sample transfer vertical through-hole.

In an example embodiment, the sample loading device may further include: a cylindrical sample loading bar that has sample grooves formed at the first intervals in a lengthwise direction and is inserted into the loading bar inserting hole. The sample may be mounted in the sample grooves.

In an example embodiment, the sample loading device may further include: a cylindrical sample transfer bar that has a single transfer groove formed on its outer circumferential surface and is inserted into the loading bar inserting hole. The sample may be mounted in the transfer groove to be transferred.

In an example embodiment, the sample transfer bar may locate the sample mounted in the transfer groove in the sample transfer vertical through-hole. The sample loading device may further include: a loading tip storage part adapted to store a standard loading tip. The loading tip storage part may be disposed below the sample transfer vertical through-hole and have an end-dented groove for transferring the sample. The sample may be mounted in the standard loading tip via the sample transfer vertical through-hole. The standard loading tip may be vertically lifted to be disposed between a top electrode and a bottom electrode for electrostatically levitating the sample.

In an example embodiment, the loading tip storage part may include: a plurality of tip storage through-holes aligned in a line; and a test tip that is mounted in the tip storage hole and has a different structure from the standard loading tip.

In an example embodiment, the test tip may include at least one of a needle-shaped needle tip for inducing a meta-stable crystal phase generated from a supercooled liquid fused liquid sample, a gas levitation loading tip that includes a nozzle disposed in its center for discharging a gas to levitate the sample and has an end-dented groove, and a quick cooling tip having a flat end.

In an example embodiment, the sample loading device may further include at least one of: a top electrode; a bottom electrode disposed to be spaced apart from the top electrode, the bottom electrode having a bottom electrode through-hole formed in its center; first to fourth auxiliary electrodes symmetrically disposed on a plane perpendicular to an axis connecting the center of the top electrode and the center of the bottom electrode to each other; a cylindrical bottom electrode support connected to the bottom electrode through-hole of the bottom electrode and made of a dielectric material; an electrode support plate on which the bottom electrode support is mounted and an auxiliary electrode support rod for supporting the auxiliary electrodes is mounted, the electrode support plate having an electrode support plate through-hole in its center; a conic collection dish disposed below the electrode support plate, the collection dish having a collection dish through-hole formed in its center; an electrode support plate support rod adapted to connect the collection dish and the electrode support plate to each other; a quenching plate disposed between the collection dish and the electrode support plate, the quenching plate having a quenching plate through-hole formed in its center; a quenching plate support rod adapted to connect the quenching plate and the collection dish to each other; a sample container support mounted on a bottom surface of the collection dish, the sample container support having a sample container through-hole formed in a horizontal direction; a dish bottom plate disposed below the sample cover part, the dish bottom plate having a trench extending in a direction perpendicular to a direction in which the sample cover part extends; and the loading tip storage part inserted into the trench and disposed between the dish bottom plate and the sample container, the loading tip storage part having a through-hole formed in its center.

In an example embodiment, the sample storage part may further include a sample container support successively connected to the sample standby part. The sample container support may have one end where a support groove formed in the center of the sample container in an extending direction of the end and may be fixed to a vacuum chamber via the support groove.

An example embodiment of the present disclosure provides an operating method of a sample loading device including a sample storage part including a cylindrical sample standby part having an external diameter of a first diameter and a cylindrical sample loading part having an external diameter of a second diameter and a cylindrical sample cover part having an external diameter of the second diameter and covering the sample standby part, wherein the sample storage part has a loading bar inserting hole that is formed in its center in a lengthwise direction. The loading bar inserting hole may be formed through the sample standby part and is formed successively through a portion of the sample loading part. The sample standby part may have sample storage vertical through-holes that are formed at regular intervals in a lengthwise direction and penetrate in a direction perpendicular to the lengthwise direction. The sample loading part may have a single sample transfer vertical through-hole that is formed on a surface where the sample storage vertical through-hole is viewed, vertically penetrates the sample loading part, and is connected to the loading bar inserting hole. A cylindrical sample loading bar may have sample holes formed at the first intervals in a lengthwise direction and is inserted into the loading bar inserting hole. A cylindrical sample transfer bar may have a single transfer groove formed on its outer circumferential surface and is inserted into the loading bar inserting hole. The operating method includes: storing samples in the sample storage vertical through-holes using the sample loading bar; removing the sample loading bar and inserting the sample transfer bar into the loading bar inserting hole; and locating one of the sample inserted into the sample storage vertical through-holes in the sample transfer vertical hole using the sample transfer bar.

An example embodiment of the present disclosure provides a sample loading device. The sample loading device may include: a rod-shaped sample standby part; a sample storage part successively connected in an extending direction of the sample standby part, the sample storage part including the sample loading part; and a sample cover part to cover the sample standby part. The sample storage part may have a loading bar inserting hole formed in its center in a lengthwise direction. The loading bar inserting hole may be formed through the sample standby part and may be formed successively through a portion of the sample loading part. The sample standby part may have vertical through-holes that have regular first intervals in a lengthwise direction and penetrate in a direction perpendicular to the lengthwise direction. The sample loading part may have a single sample transfer vertical through-hole. The sample transfer vertical through-hole may be formed on a surface where the sample storage vertical through-hole is viewed, may penetrate the sample loading part, and may be connected to the loading bar inserting hole.

An example embodiment of the present disclosure provides an operating method of a sample loading device. The operating method includes: storing samples in sample storage vertical through-holes using a sample loading bar at a sample container that has a single sample transfer vertical through-hole and the sample storage vertical through-holes spaced apart from the sample transfer vertical through-hole and formed at regular intervals, has a loading bar inserting hole formed in its center in an extending direction, and has an outer circumferential surface covered with a cover; removing the sample loading bar and inserting the sample transfer bar into the loading bar inserting hole; and locating one of the sample inserted into the sample storage vertical through-holes in the sample transfer vertical hole using the sample transfer bar.

An example embodiment of the present disclosure provides an electrostatic levitation apparatus. The electrostatic levitation apparatus includes: a sample container that has a single sample transfer vertical through-hole and the sample storage vertical through-holes spaced apart from the sample transfer vertical through-hole and formed at regular intervals, has a loading bar inserting hole formed in its center in an extending direction, and has an outer circumferential surface covered with a cover; and a loading tip storage part adapted to store a standard loading tip for transferring a sample. The standard loading tip may be disposed between a top electrode and a bottom electrode for vertically lifting a sample disposed in the sample transfer vertical through-hole to electrostatically levitate the sample.

An example embodiment of the present disclosure provides an electrostatic levitation apparatus. The electrostatic levitation apparatus include: a top electrode; a bottom electrode disposed to be vertically spaced apart from the top electrode, the bottom electrode having a bottom electrode through-hole formed in its center; and a loading tip storage part adapted to store a standard loading tip and a test tip for transferring a sample between the top electrode and the bottom electrode, the loading tip storage part having a plurality of loading tip storage through-holes aligned in a line. The loading tip storage part may perform a linear motion in a direction in which the loading tip storage through-holes are aligned.

In an example embodiment, the test tip may be a sharp-needle-type needle tip to induce a predetermined crystal structure from a supercooled fused liquid sample of a meta-stable state.

In an example embodiment, the test tip may control crystallization speed of a supercooled fused liquid sample.

In an example embodiment, the test tip may be a quick cooling tip having a flat end.

In example embodiment, the electrostatic levitation apparatus may further include: a sample container having a single sample transfer vertical through-hole and a plurality of sample storage vertical through-holes spaced apart from the sample transfer vertical through-hole and formed in regular intervals, having a loading bar inserting hole formed in its center in an extending direction, and having an outer circumferential surface covered with a cover.

In an example embodiment, the electrostatic levitation apparatus may further include: a dish bottom plate on which the loading tip storage part is mounted. The dish bottom plate may have a trench formed in its one surface, and the loading tip storage part may be inserted into the trench to perform a rectilinear motion.

In an example embodiment, the electrostatic levitation apparatus may further include at least one of: first to fourth auxiliary electrodes symmetrically disposed on a plane perpendicular to an axis connecting the center of the top electrode and the center of the bottom electrode to each other; a cylindrical bottom electrode support connected to the bottom electrode through-hole of the bottom; an auxiliary electrode support rod for supporting the auxiliary electrodes is mounted, the electrode support plate having an electrode support plate through-hole in its center; a conic collection dish disposed below the electrode support plate, the collection dish having a collection dish through-hole formed in its center; a sample container support mounted on a bottom surface of the collection dish, the sample container support having a sample container through-hole in a horizontal direction; a sample container inserted into the sample container through-hole; and a dish bottom plate disposed below the sample cover part, the dish bottom plate having a trench extending in a direction perpendicular to a direction in which the sample cover part extends.

An embodiment of the present disclosure provides an operating method of an electrostatic levitation apparatus. The operating method includes: locating a sample between a top electrode and a bottom electrode using a standard loading tip having an end-dented groove for transferring the sample; applying an electric field between the top electrode and the bottom electrode to electrostatically levitate the sample; heating and fusing the electrostatically levitated sample using a heating laser; remove the heating laser to radiantly cool the sample; and contacting a sharp-needle-type needle tip for inducing a predetermined crystal structure from a supercooled fused liquid sample with the supercooled fused liquid sample.

An embodiment of the present disclosure provides an operating method of an electrostatic levitation apparatus. The operating method may include: locating a sample between a top electrode and a bottom electrode using a standard loading tip having an end-dented groove for transferring the sample; applying an electric field between the top electrode and the bottom electrode to electrostatically levitate the sample; heating and fusing the electrostatically levitated sample using a heating laser; and contacting a sharp-needle-type needle tip for controlling crystallization speed of a supercooled fused liquid sample with the supercooled fused liquid sample.

An embodiment of the present disclosure provides an operating method of an electrostatic levitation apparatus. The operating method may include: locating a sample between a top electrode and a bottom electrode using a standard loading tip having an end-dented groove for transferring the sample; applying an electric field between the top electrode and the bottom electrode to electrostatically levitate the sample; heating and fusing the electrostatically levitated sample using a heating laser; locating a quick cooling tip having a flat end below eh sample; and removing the electric field applied between the top electrode and the bottom electrode to drop the sample on the quick cooling tip.

An embodiment of the present disclosure provides a manufacturing method of a single crystal. The manufacturing method includes: locating a sample between a top electrode and a bottom electrode using a standard loading tip having an end-dented groove for transferring the sample; applying an electric field between the top electrode and the bottom electrode to electrostatically levitate the sample; heating and fusing the electrostatically levitated sample using a heating laser; removing the heating laser to radiantly cool the sample; contacting a sharp-needle-type needle tip for inducing a predetermined crystal structure from a supercooled fused liquid sample with the supercooled fused liquid sample; and crystallizing the supercooled fused liquid sample through phase transition.

An embodiment of the preset disclosure herein provides a levitation apparatus. The levitation apparatus includes: a conic collection dish having a collection dish through-hole; a sample container support disposed on a bottom surface of the collection dish, the sample container having a sample container through-hole in a horizontal direction; a sample container inserted into the sample container through-hole; a dish bottom plate disposed below the sample container, the dish bottom plate having a trench extending in a direction perpendicular to a direction in which the sample container extends on a top surface of the dish bottom plate; and a loading tip storage part adapted to store a gas levitation loading tip including a nozzle for transferring a sample to an upper portion of the collection dish and inserted into the trench.

An embodiment of the present disclosure provides an operating method of a levitation apparatus including a conic collection dish having a collection dish through-hole, a sample container support disposed on a bottom surface of the collection dish, the sample container having a sample container through-hole in a horizontal direction, a sample container inserted into the sample container through-hole, a dish bottom plate disposed below the sample container, the dish bottom plate having a trench extending in a direction perpendicular to a direction in which the sample container extends on a top surface of the dish bottom plate, and a loading tip storage part adapted to store a gas levitation loading tip including a nozzle for transferring a sample to an upper portion of the collection dish and inserted into the trench. The operating method includes: levitating a sample using the gas levitation loading tip; heating and fusing the levitated sample using a heating laser; and removing the heating laser to radiantly cool the sample.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

FIG. 2A is a perspective view of a sample container and a loading tip storage according to an embodiment of the present disclosure.

DETAILED DESCRIPTION

Preferred embodiments of the present disclosure will be described below in more detail with reference to the accompanying drawings. The present disclosure may, however, be embodied in different forms and should not be constructed as limited to the embodiments set forth herein. Rather, these embodiments are provided so that this disclosure will be thorough and complete, and will fully convey the scope of the present disclosure to those skilled in the art. Like numbers refer to like elements throughout.

A sample charged under a high vacuum may be levitated by an electrostatic field between two electrodes.

In order to stably levitate a levitated sample at a given position, an electric field or a voltage is controlled in X, Y, and Z directions depending on position variation of the levitated sample.

A sample container and various tips are required to perform various tests on a plurality of samples. The samples may be contained in the sample container, and the various tests may be performed on a sample transferred from the sample container.

A sample loading device according to an embodiment of the present disclosure may include a tip which is capable of sequentially electrostatically levitating a plurality of samples and performing various tests on each of the samples.

Figure 1A:
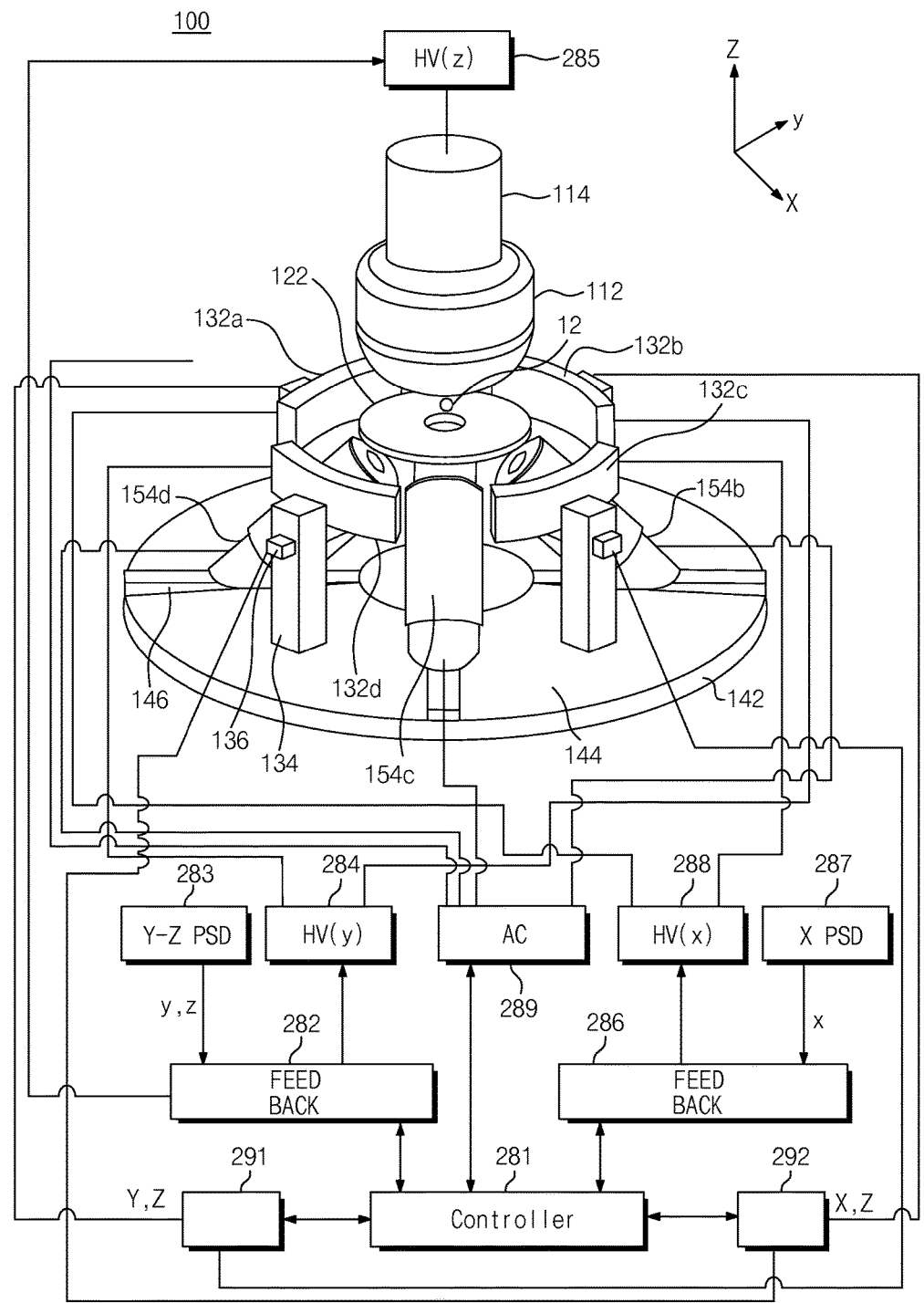
FIG. 1A is a perspective view of an electrostatic levitation apparatus according to an embodiment of the present disclosure.

FIG. 1A is a perspective view of an electrostatic levitation apparatus according to an embodiment of the present disclosure.

Figure 1B:
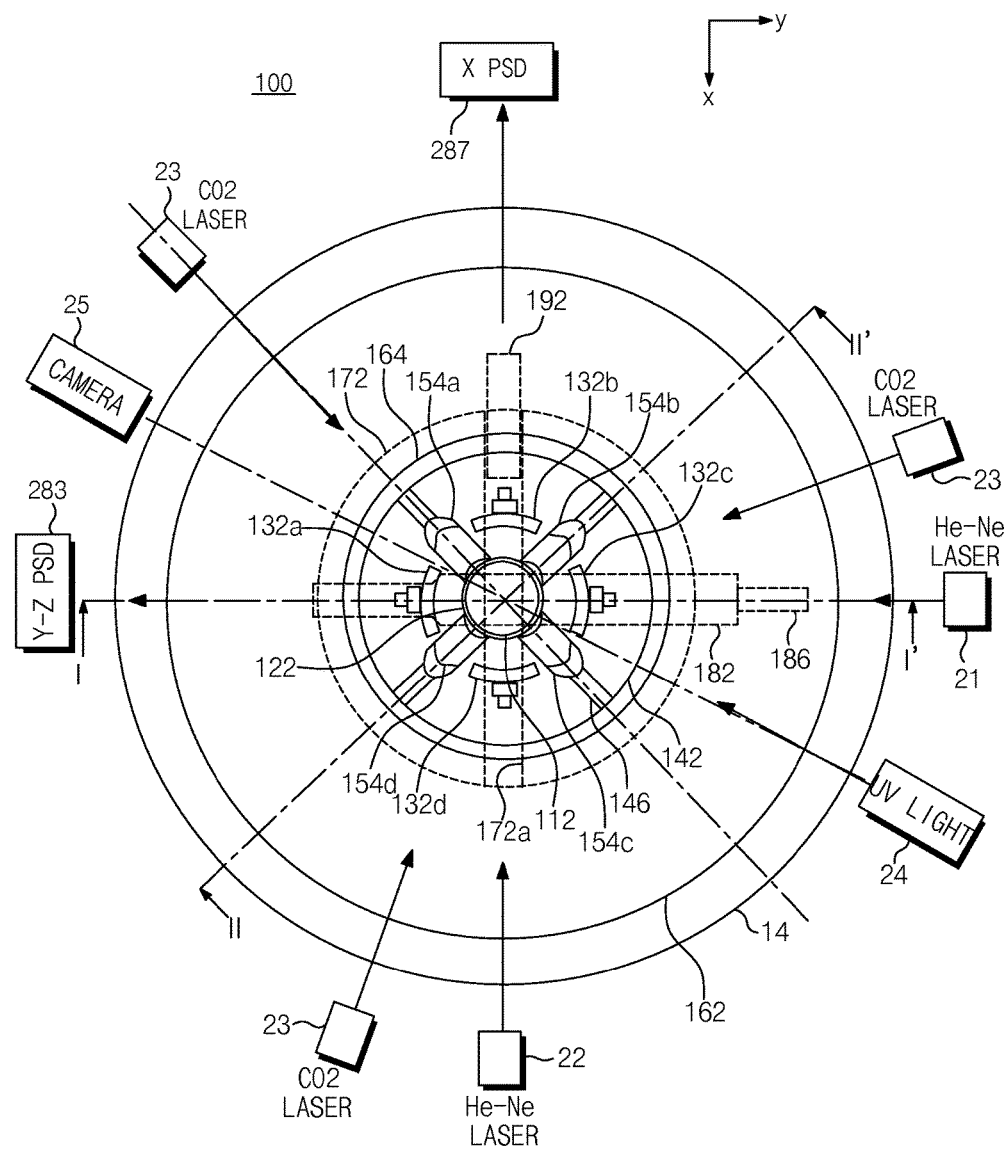
FIG. 1B is a top plan view of the electrostatic levitation apparatus in FIG. 1A.

FIG. 1B is a top plan view of the electrostatic levitation apparatus in FIG. 1A.

Figure 1C:
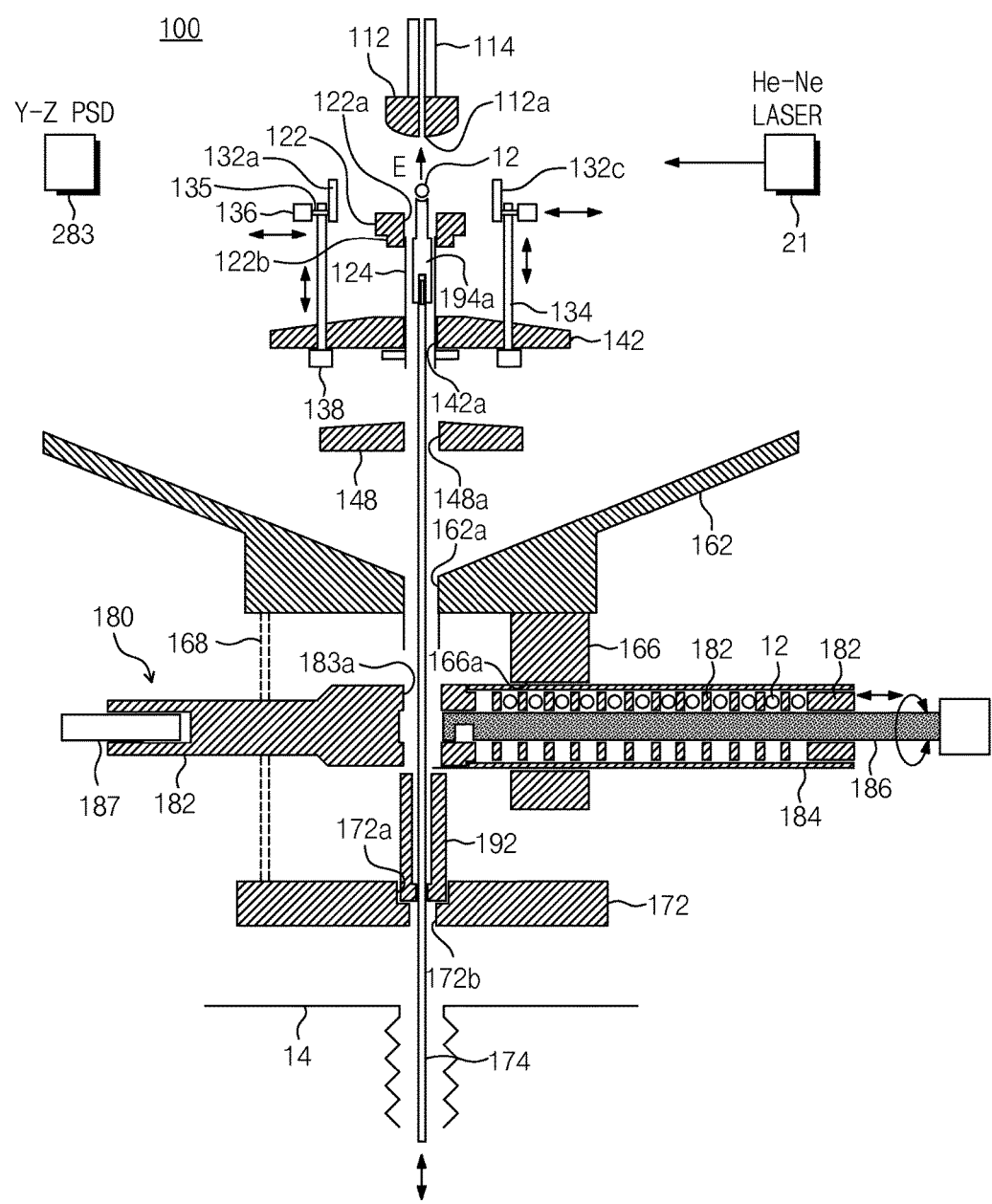
FIG. 1C is a cross-sectional view taken along the line I-I' in FIG. 1B.

FIG. 1C is a cross-sectional view taken along the line I-I' in FIG. 1B.

Figure 1D:
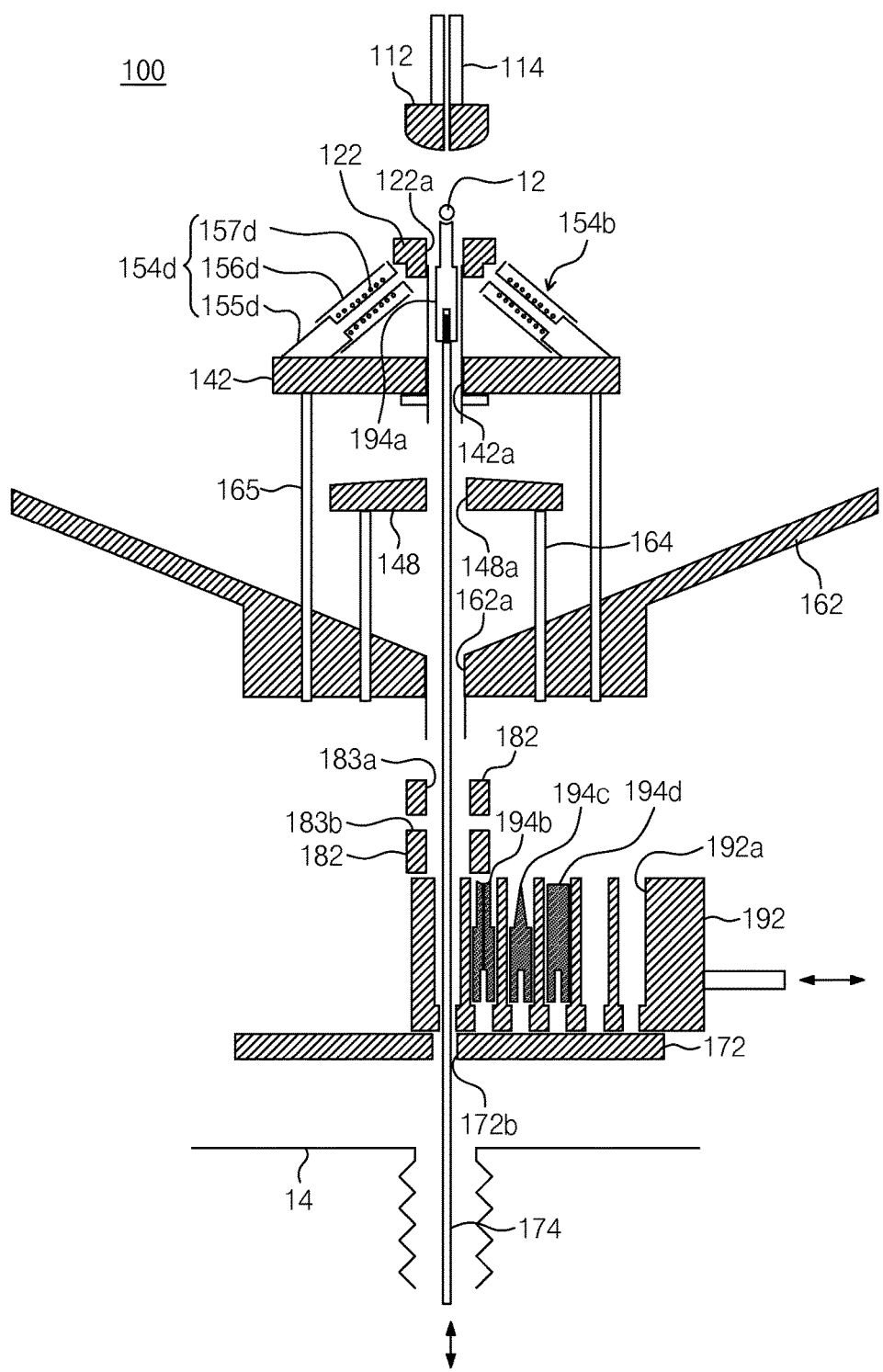
FIG. 1D is a cross-sectional view taken along the line II-II' in FIG. 1B.

FIG. 1D is a cross-sectional view taken along the line II-II' in FIG. 1B.

FIG. 2A is a perspective view of a sample container and a loading tip storage according to an embodiment of the present disclosure.

Figure 2B:
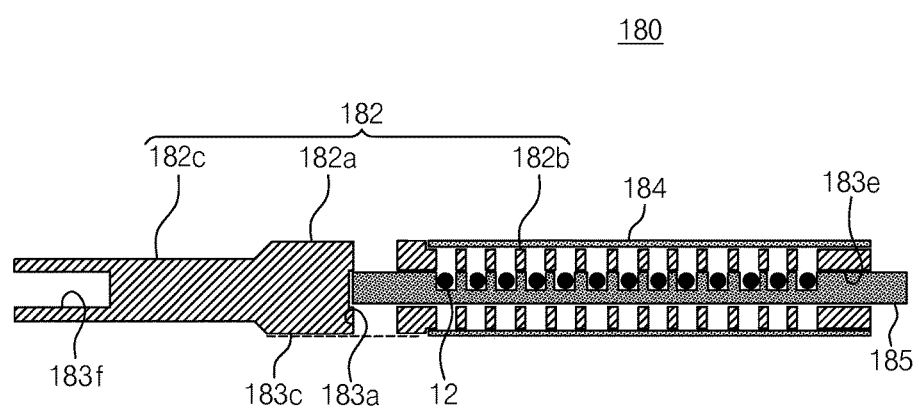
FIG. 2B is a cross-sectional view of the sample container in FIG. 2A.

FIG. 2B is a cross-sectional view of the sample container in FIG. 2A.

Referring to FIGS. 1 and 2, an electrostatic levitation apparatus 100 includes a top electrode 112, a bottom electrode 122 spaced vertically apart from the top electrode 112, and first to fourth auxiliary electrodes 132a to 132d disposed symmetrically on an xy plane perpendicular to an z-axis connecting the center of the top electrode 112 and the center of the bottom electrode 122 to each other. A sample 12 is levitated between the top electrode 112 and the bottom electrode 122.

The electrostatic levitation apparatus 100 may be disposed inside a cylindrical vacuum chamber 14. The vacuum chamber 14 may be exhausted at ultrahigh vacuum of millitorr (mTorr) or less. The vacuum chamber 14 may include a plurality of windows. A heating laser 23 may be disposed outside the window of the vacuum chamber 14 to heat the sample 12. The heating laser 23 may be carbon dioxide ($CO_2$) lasers arranged at an angle of 120 degrees.

The sample 12 may be charged with positive charges. As the sample 12 is heated by the heating laser 23, the sample 12 may lose its charges. Thus, a UV light source 24 may be irradiated to the sample 12 to provide the lost charges. UV light emits electrons based on the photoelectric effect to charge the sample 12 with positive charges. A camera 25 may be mounted on the vacuum chamber 14 at the side opposite to the UV light source 24.

The sample 12 may be levitated between the top electrode 112 and the bottom electrode 122, and an x-axis position of the sample 12 may be measured by an x-axis position sensitive detector (PSD) 287. The x-axis position sensitive detector 287 may be a device to measure a light position in a one or two-dimensional space. The x-axis position sensitive detector 287 and an x-axis probe light source 22 may be disposed on a diagonal around the sample 12 to face each other. The x-axis probe light source 22 may be an He—Ne laser.

In order to a y-axis position and a z-axis position, a Y-Z position sensitive detector 283 and a second probe light source 21 may be disposed on a diagonal around the sample 12 to face each other. The second probe light source 21 may be an He—Ne laser. The first probe light source 22 and the second probe light source 21 may be disposed at an interval of 90 degrees. A position sensitive detector may measure a position of the sample 12 through a shadow image of a probe light source.

A measuring result of the x-axis position sensitive detector 287 may be provided to a first feedback controller 286, and a measuring result of the Y-Z position sensitive detector 283 may be provided to a second feedback controller 282. The first feedback controller 286 may provide a first control signal to an x-axis high voltage generator 288 to control the x-axis position of the sample 12. The second feedback controller 282 may provide a second control signal to a y-axis high voltage generator 284 to control a y-axis position of the sample 12. The second feedback controller 282 may provide a third control signal to a z-axis high voltage generator 285 to control a z-axis position of the sample 12.

When the sample 12 is a conductor, induction coil parts 154a to 154d may be disposed between the auxiliary electrodes 132a to 132d to provide a rotary motion produced by induced electromotive force. The induction coil parts 154a to 154d may be disposed around the sample 12 to face each other.

The first and third induction coil parts 154a and 154c facing each other may be electrically connected in series to each other. The second and fourth induction coil parts 154b and 154d facing each other may be electrically connected in series to each other. An alternating current (AC) power supply 289 may apply AC current to the first to fourth induction coils 154a to provide the induced electromotive force to the sample 12. Thus, the conductive sample 12 may be rotated.

The auxiliary electrodes 132a to 132d may perform a horizontal motion and a vertical motion. The first to fourth auxiliary electrodes 132a to 132d may be arranged clockwise. The horizontal motion of the auxiliary electrodes 132a to 132d may be provided by a horizontal actuator 136. The vertical motion of the auxiliary electrodes 132a to 132d may be provided by a vertical actuator 138. An x-axis horizontal actuator driver 292 may control the x-axis horizontal actuator 136, and a y-axis horizontal actuator driver 291 may control the y-axis horizontal actuator 136. The x-axis horizontal actuator 136 may adjust positions in an x-axis direction of the first and third auxiliary electrodes 132a and 132c. The y-axis horizontal actuator 136 may adjust positions in a y-axis direction of the second and fourth auxiliary electrodes 132b and 132d.

A controller 281 may control the first feedback controller 285, the second feedback controller 282, the x-axis horizontal actuator driver 292, the y-axis horizontal actuator driver 291, and the AC power supply 289. Thus, the sample 12 may not fall on a predetermined position and may be electrostatically levitated stably.

The top electrode 112 may be in the form of a disc-shaped flat plate, and a corner of the upper electrode 112 may be rounded. The top electrode 112 may be connected to the z-axis high voltage generator 285. The top electrode 112 may be made of copper. The top electrode 112 may be supported by a top electrode support 114.

The top electrode support 114 may be made of a dielectric material. A top electrode through-hole 112a may be formed in the center of the top electrode 112. The top electrode through-hole 112a may be used to align the top electrode 112 with the bottom electrode 122. A high voltage of the z-axis high voltage generator 285 may be applied to the top electrode 112 through the top electrode support 114. Thus, an electric field may be established in a direction opposite to a gravity direction.

The bottom electrode 122 may be aligned with the top electrode 112 and may be vertically spaced apart from the top electrode 112 in the z-axis. A bottom electrode through-hole 122a may be formed in the center of the bottom electrode 122. The sample 12 may be supplied through the bottom electrode through-hole 122a. The bottom electrode 122 may be in the form of a disk, and a corner of the bottom electrode 122 may be rounded. The bottom electrode 122 may include a cylindrical extension 122b extending in the z-axis direction. A screw hole may be formed on an inner surface of the extension 122b.

A bottom electrode support 124 may be made of a dielectric material and have a center in which a bottom electrode support through-hole is formed. The bottom electrode support 124 may be connected to the bottom electrode through-hole 122a and may be cylindrical. A screw thread may be formed on an outer surface of one end of the bottom electrode support 124. A washer-shaped washer part 124a may be fixedly connected with a bottom surface of an electrode support plate 142. The bottom electrode support 124 may be made of ceramic or alumina material.

The electrode support plate 142 may be equipped with the bottom electrode support 124 and an auxiliary electrode support rod 134 to support the auxiliary electrodes 132a to 132d. The electrode support plate 142 may have the center in which an electrode support plate through-hole 142a is formed. One end of the bottom electrode support 124 may be connected with the bottom electrode 122 through the electrode support plate through-hole 142a. A top surface of the electrode support plate 142 may be in the form of a truncated cone having a fixed slope. A bottom surface of the electrode support plate 142 may be a plane. An upper center portion of the electrode support plate 142 may be a plane. A diameter of the upper center portion may be substantially equal to that of the bottom electrode 122. The electrode support plate 142 may include a cross-shaped protrusion 146. A top surface of the protrusion 146 may constitute a horizontal plane.

Four auxiliary electrode supports 134 may be symmetrically mounted on the electrode support plate 142 in the x-axis direction and the y-axis direction around the sample 12. The auxiliary electrode support 134 may be disposed through the electrode support plate 142. The auxiliary electrode support 134 may be fixed to a bottom surface of the electrode support plate 142. A vertical actuator 138 may be mounted on the bottom surface of the electrode support plate 142. The vertical actuator 138 may provide a vertical motion to the auxiliary electrode support 134.

A horizontal support 135 may be connected to an auxiliary electrode 132a through an upper end portion of the auxiliary electrode support 134. The horizontal support 135 may be connected to the horizontal actuator 138. The horizontal actuator 138 may provide a horizontal motion to the auxiliary electrode 132a. The horizontal actuator 138 may be a piezoelectric element or a piezoelectric motor. A first auxiliary electrode 132a and a third auxiliary electrode 132c may be disposed around the sample 12 in the x-axis direction to face each other. A second auxiliary electrode 132b and a fourth auxiliary electrode 132d may be disposed around the sample 12 in the y-axis direction to face each other.

The auxiliary electrodes 132a to 132d may be in the form of a 4-split circular cylindrical shell. Inner side surfaces and outer side surfaces of the auxiliary electrodes 132a to 132d may each have a fixed curvature. The curvature may be equal to a radius of a position where the auxiliary electrode is disposed on the basis of the center of the bottom electrode 122. Each of the auxiliary electrodes 132a to 132d may be made of copper. A pair of auxiliary electrodes may concentrate a line of electric force to the sample 12. Thus, stable position control of the sample 12 may be accomplished. A vertical position of the auxiliary electrode may be adjusted according to a vertical position of the sample 12. More specifically, as a charge-containing gas is jetted during fusion of the sample 12, a vertical position of the sample 12 may be varied. In this case, the auxiliary electrode may move according to the vertical position of the sample 12. Thus, stable vertical position control of the sample 12 may be accomplished.

The beam of the heating laser 23 and the center of the bottom electrode 122 may be misaligned with each other. In this case, a pair of auxiliary electrodes may move in the x-axis direction or the y-axis direction while being maintained at a regular interval. The sample 12 may not be levitated in the center of the top electrode 112 but may be levitated at various horizontal positions. Thus, time for the alignment of the heating laser 23 may be reduced.

It is difficult to minutely adjust outputs of the x-axis high voltage generator 288 and the y-axis high voltage generator 284. Therefore, it is difficult to minutely adjust the intensity of an electric field between the pair of auxiliary electrodes. In order to overcome this, a distance between the pair of auxiliary electrodes may be adjusted. Thus, the intensity of the electric field between the pair of auxiliary electrodes may be minutely adjusted. As a result, stable horizontal position control of the sample 12 may be accomplished.

The induced coil parts 154a to 154d may be disposed at the cross-shaped protrusion 146 of the electrode support plate 142. The induced coil parts 154a to 154d may include an induced coil 157d, a coil bobbin 155d on which the induced coil 157d is wound, and a coil bobbin cover 156d covering the coil bobbin 155d. The induced coil parts 154a to 154d may include first to fourth induced coil parts 154a to 154d.

The first induced coil part 154a may be disposed between the first auxiliary electrode 132a and the second auxiliary electrode 132b, the second induced coil part 154b may be disposed between the second auxiliary electrode 132b and the third auxiliary electrode 132c, the third induced coil part 154c may be disposed between the third auxiliary electrode 132c and the fourth auxiliary electrode 132d, and the fourth induced coil part 154d may be disposed between the fourth auxiliary electrode 132d and the first auxiliary electrode 132a. The coil bobbin 155d may slope toward the bottom electrode 122. The induced coil parts 154a to 154d may provide a rotational force to a conductive sample.

A collection dish 162 may be disposed below the electrode support plate 142, may have a collection dish through-hole 152a formed in its center, and may have a cone shape. The collection dish 162 and the electrode support plate 142 may be fixed by an electrode support plate support rod 165. A top surface of the collection dish 162 may have a conic shape. A central bottom surface of the collection dish 162 may be a plane, and an outside bottom surface of the collection dish 162 may have a conic shape. The outside of the collection dish 162 may be in the form of a dish having a fixed thickness. The collection dish 162 may re-collect a fallen sample. The fallen sample may be collected to a sample container 180 through the collection dish through-hole 152a.

A sample container support 116 may be disposed on a bottom surface of the collection dish 162 and may have a sample container through-hole 166a formed in a horizontal direction.

A quenching plate 148 may be disposed between the collection dish 162 and the electrode support plate 142 and may have a quenching plate through-hole 148a formed in its center. A top surface of the quenching plate 148 may be rounded. Specifically, the top surface of the quenching plate 148 may have a truncated conic shape. A quenching plate support rod 164 may connect and fix the quenching plate 148 and the collection dish 162 to each other.

The sample container 180 may be inserted into the sample plate through-hole 166a. The sample container 180 may include a sample storage part 182 and a sample cover part 184. The sample storage part 182 may include a sample standby part 182b, a sample loading part 182a, and a sample container support 182c that are successively connected. The sample container 182 may contain the sample 12 and provide the sample 12 between the top electrode 112 and the bottom electrode 122. An electrostatically levitated sample may be heated to be fused through the heating laser 23.

The sample standby part 182b may be in the form of a rod. The sample loading part 182a may be successively connected in an extending direction of the sample standby part 182b and may be in the form of a rod. The sample cover part 184 may have a shape to cover the sample standby part 182b.

The sample storage part 182 may have a loading bar inserting hole 183e formed in its center in a lengthwise direction. The loading bar inserting hole 183e may be formed in a lengthwise direction of the sample standby part 182b and may be formed successively through a portion of the sample loading part 182a. A diameter of the sample loading part 182a may be substantially equal to an internal diameter of the sample cover part 184.

The sample standby part 182b may have sample storage vertical through-holes 183d that are formed at regular first intervals in a lengthwise direction and penetrate the sample standby part 182b in a direction perpendicular to the lengthwise direction. The sample standby part 182b may be in the form of a cylinder having an external diameter of a first diameter. A diameter of each of the sample storage through-holes 183d may be greater than that of the sample 12. A screw thread may be formed on an outer circumferential surface of one end of the sample standby part 182b.

The sample loading part 182a may be in the form of a cylinder having an external diameter of a second diameter greater than the first diameter. The sample loading part 182a may have a single sample transfer vertical through-hole 183a. The sample transfer vertical through-hole 183a may be formed on a surface where the sample storage vertical through-hole 183d is viewed, may vertically penetrate the sample loading part 182a, and may be connected to the loading bar inserting hole 183e. One surface where the sample transfer vertical through-hole 183a of the sample loading part 182a is exposed may include a plane part 183c processed as a plane. The sample container 180 may perform a rotary motion such that the plane part 183c faces downwardly or upwardly.

A slit 183b may be formed on both side surfaces of the sample loading part 182a in a direction perpendicular to a direction in which the sample transfer vertical through-hole 183a is formed. The slit 183b may be connected to the sample transfer vertical through-hole 1823a. The slit 183b may be used to check whether the sample 12 is mounted, with the naked eye or laser beam.

The sample container support 182c may have one end where a support groove 183f formed in the center of the sample container support 182c in an extending direction of the end. A connection part 187 may be inserted into the support groove 183f and may be fixed to a vacuum chamber.

The sample cover part 184 may have a shape to cover the sample standby part 182d. The sample cover part 184 may be in the form of a cylinder shell. An internal diameter of the sample cover part 184 may be equal to an external diameter of the sample standby part 182b. A screw groove may be formed on an inner circumferential surface of one end of the sample cover part 184. The screw groove may be combined with the screw thread of the sample standby part 182b to be fixed. An external diameter of the sample cover part 194 may be substantially equal to that of the sample loading part 182a.

The sample loading bar 185 may be in the form of a cylinder, may have sample grooves 185a are formed in the first intervals, and may be inserted into the loading bar inserting hole 183e. The sample 12 may be mounted in the sample grooves 185a.

A sample transfer bar 186 may be in the form of a cylinder, may have a single transfer groove 186a formed on its outer circumferential surface, may be inserted into the loading bar inserting hole 182e, and may perform a linear motion and a rotary motion. The sample 12 may be transferred while being mounted in the transfer groove 186a. The sample transfer bar 186 may locate the sample 12 mounted in the transfer groove 186a into the sample transfer vertical through-hole 183a.

A loading tip storage part 192 may store a standard loading tip 194a disposed below the sample transfer vertical through-hole 183a. The standard loading tip 194a may have an end-dented groove for transferring the sample 12. The sample 12 may be mounted on the standard loading tip 194a via the sample transfer vertical through-hole 183a. The standard loading tip 194a may be vertically lifted by a vertical transfer part 174 to be disposed between the top electrode 112 and the bottom electrode 122 for electrostatically levitating the sample 12.

The loading tip storage part 192 may have a plurality of loading tip storage through-holes 192a aligned in a line and one or more test tips 194b to 194d having different structures mounted in the loading tip storage through-holes 192a. The loading tip storage part 192 may in the form of a rectangular parallelepiped. The loading tip storage through-holes 192a may be formed to be aligned in a lengthwise direction of the loading tip storage part 192. The loading tip storage through-hole 192a may have an upper through-hole having a first diameter and a lower through-hole having a second diameter smaller than the first diameter. The upper through-hole and the lower through-hole may be vertically aligned with each other to be continuously disposed.

A dish bottom plate 172 has a trench 172a formed on its top surface to extend in a direction perpendicular to a direction in which the sample container 180 extends. A dish bottom plate through-hole 172b is formed in the center of the trench 172a. The loading tip storage part 192 is movable along the trench 172a of the dish bottom plate 172. A horizontal moving part mounted at the vacuum chamber 14 may be connected with a side surface of the loading top storage part 192 to move the loading tip storage part 192. As the loading tip storage part 192 moves along the trench 172a, various test tips may be selected. The collection dish 162 may be fixed to the dish bottom plate 172 via a collection dish support rod. The dish bottom plate 172 may be fixed to the vacuum chamber 14.

The vertical transfer part 174 may vertically transfer the standard loading tip 194a or the test tip via the dish bottom plate through-hole 172b formed in the center of the dish bottom plate 172.

The test tips 194b to 194d may include at least one of a needle tip 194c having a sharp needle shape to induce meta-stable crystallization that may arise from a supercooled liquid fused liquid sample, a gas levitation loading tip 194b including a gas injection nozzle disposed in its center to levitate the sample 12, and a quenching tip 194d having a flat end.

The standard loading tip 194a may include a cylindrical first portion having a first diameter and a cylindrical second portion having a second diameter. The second diameter is greater than the first diameter. The end of the first portion may be dented to mount the sample 12 thereon. A groove may be formed at the end of the second portion and the end of the vertical transfer part 174 may be inserted into the groove. Thus, the vertical transfer part 174 may vertically transfer the stand loading tip 194a and the sample 12.

By removing a heating laser beam after an electrostatically levitated sample is fused using the heating laser, the fused sample may become a supercooled state (a state in which a liquid is maintained at a liquid state in a temperate area of a solid). The supercooled state is a meta-stable liquid state, in which a material having new structure and properties may be discovered.

In a conventional crystal growing device using a contact-type container, a crucible for containing a fused liquid may cause contamination and influx of contaminants. Moreover, the crucible itself may cause heterogeneous nucleation. Therefore, it is difficult to discover a material having new properties through high-purity single crystal growth or supercooling. As a result, in a contact-free levitated state, a supercooled liquid of the meta-stable state may be used to develop a material having new structure and properties.

A method for discovering a new crystalline phase or growing a single crystal from an electrostatically levitated fused liquid sample is proposed.

Different crystal types of probes are mounted to induce a meta-stable crystal that may be formed from a supercooled fused liquid sample. The needle tip 194c may have a predetermined crystal structure. For example, the needle tip 194c may have a body-centered cubic (BCC) lattice structure, a face-centered cubic (FCC) lattice structure or a hexagonal closed-packed (HCP) structure. The needle tip 194c having a predetermined crystal structure may come in contact with the supercooled fused liquid sample, and the supercooled fused liquid sample may be crystallized to have a crystal structure that the needle tip 194c induces. A needle tip 194c having a BCC structure may be used to induce the sample to a crystal having the BCC structure. In addition, a needle tip 194c having an FCC structure may be used to induce the sample to a crystal having the FCC structure.

The needle tip 194c may include a cylindrical first portion having a first diameter and a conic second portion. The conic second portion may have a predetermined crystal structure.

The needle tip 194c may be charged with the same positive charges as a charged state of the sample 12. In addition, the needle tip 194c is downwardly movable while rotating to induce predetermined crystal growth. The vertical transfer part 174 may additionally provide a rotary motion of the needle tip 194c. The needle tip 194c may induce a meta-stable crystal phase and generate single-crystal growing and single-crystal seeds in a supercooled liquid state. According to the degree of supercooling, the needle tip 194c may come in contact with a supercooled liquid to adjust crystallization speed and a crystal microstructure.

The quenching tip 194d may be in the form of a cylinder having a fixed diameter. One end of the quenching tip 194d is a plane, and a groove for combination with the vertical transfer part 174 may be formed at the other end of the quenching tip 194d. The quenching tip 194d may be used to quickly cool the electrostatically levitated sample. More specifically, the quenching tip 194d may be vertically lifted by the vertical transfer part 174 at the same height as the quenching plate 148. Then, the sample 12 may fall on the quenching tip 194d by removing a voltage between the top electrode 112 and the bottom electrode 122 of the electrostatic levitation apparatus 100. A calorimeter disposed around the quenching plate 148 may measure a procedure of quickly cooling the sample 12 by the quenching tip 194d. Before the sample 12 falls on the quenching tip 194d, the sample 12 may be cooled to be a solid state. The quenching tip 194d may quickly cooling the sample 12 to provide a meta-stable crystal phase. The solid-state sample may be quickly cooled by the quenching tip 194d.

The gas levitation loading tip 194b has a similar structure to the standard loading tip 194a. However, the gas levitation loading tip 194b includes a nozzle disposed in its center. Accordingly, a gas may be provided through the nozzle to levitate the sample 12. The gas may be provided through the pipe-shaped vertical transfer part 174.

According to an embodiment of the present disclosure, a cartridge for loading sample may decrease in size. Thus, a vacuum chamber may decrease in size and a vacuum state of the vacuum chamber may be obtained within a short period of time. As a result, time required for a test may be reduced.

After a test is performed, a sample may be collected to an original cartridge. Thus, loss of the sample may be prevented. Moreover, the sample may always be collected to an original position due to a collection dish.

Hereinafter, an operating method of a sample loading device will now be described in detail with reference to accompanying drawings.

Figure 3A:
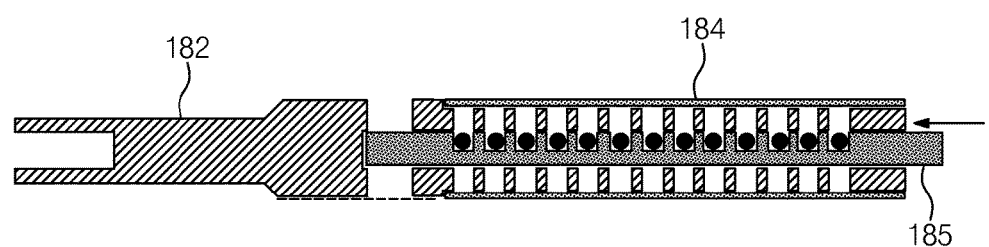
FIGS. 3A through 3Q illustrate an operating method of a sample loading device according to an embodiment of the present disclosure.
Figure 3B:
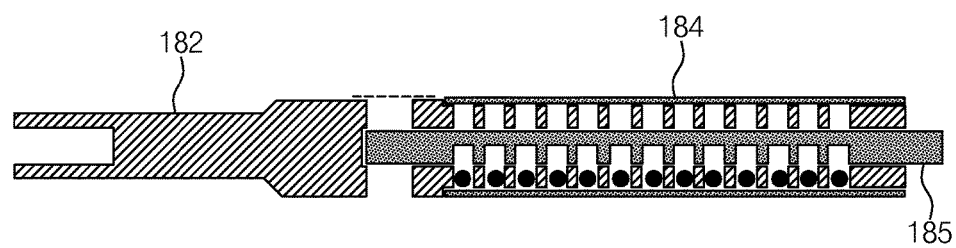
Figure 3C:
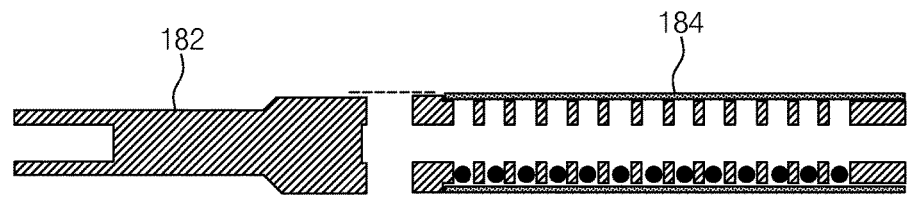
Figure 3D:
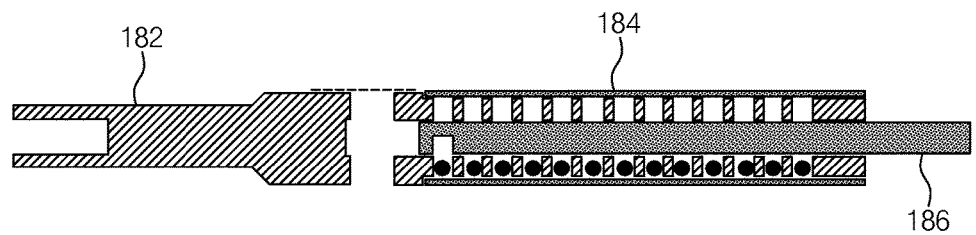
Figure 3E:
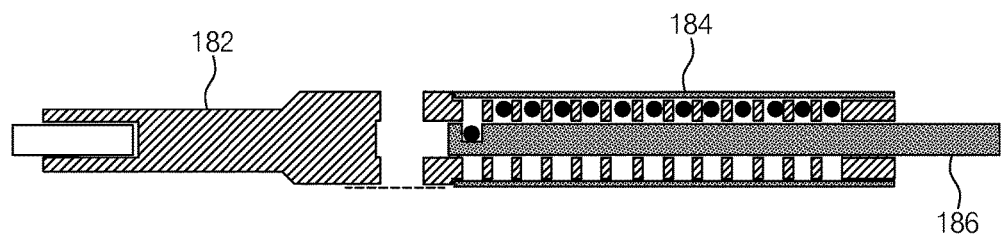
Figure 3F:
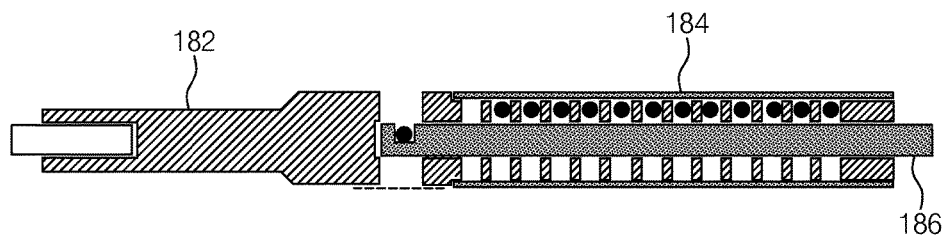
Figure 3G:
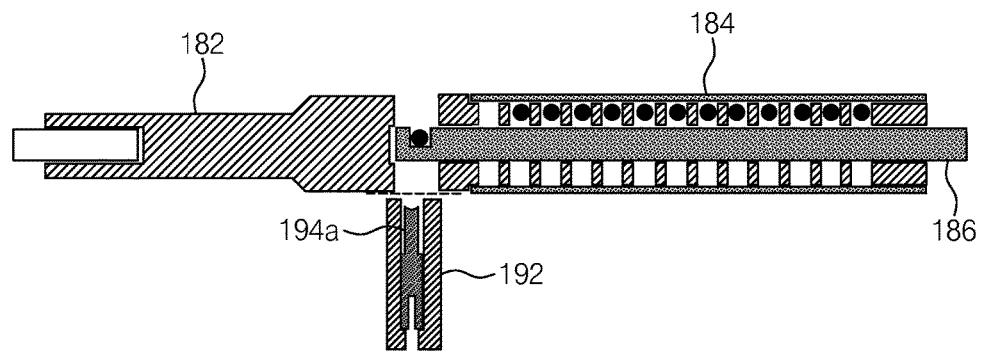
Figure 3H:
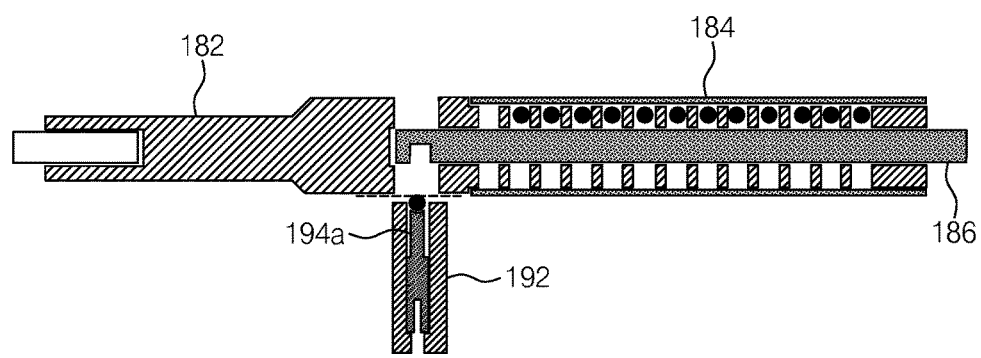
Figure 3I:
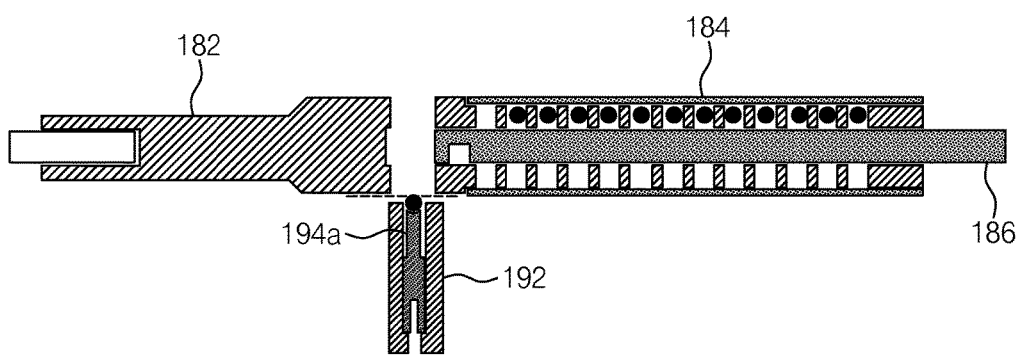
Figure 3J:
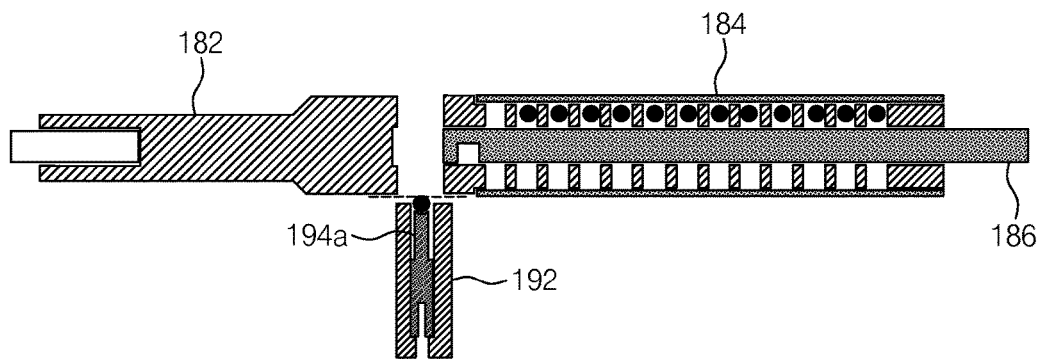
Figure 3K:
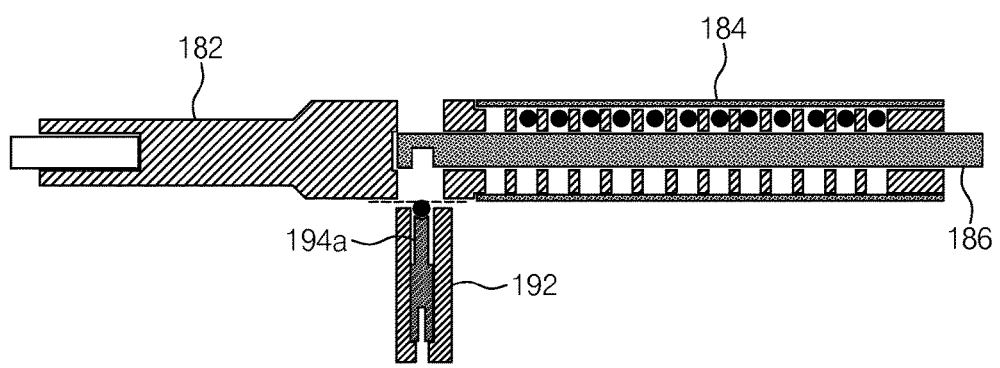
Figure 3L:
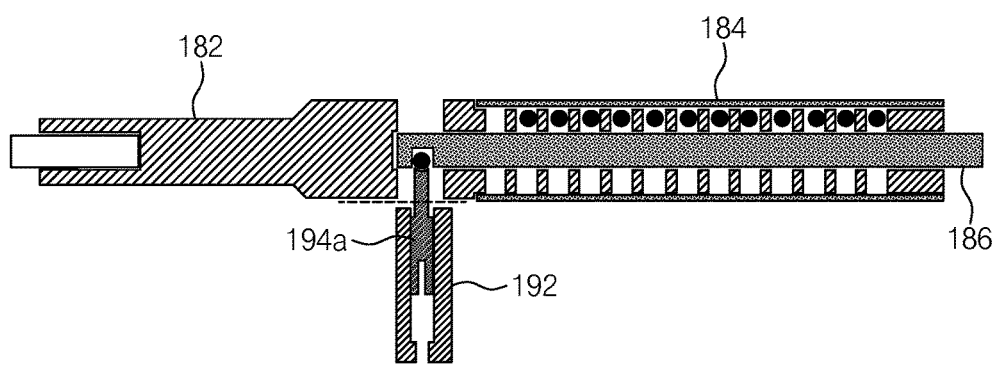
Figure 3M:
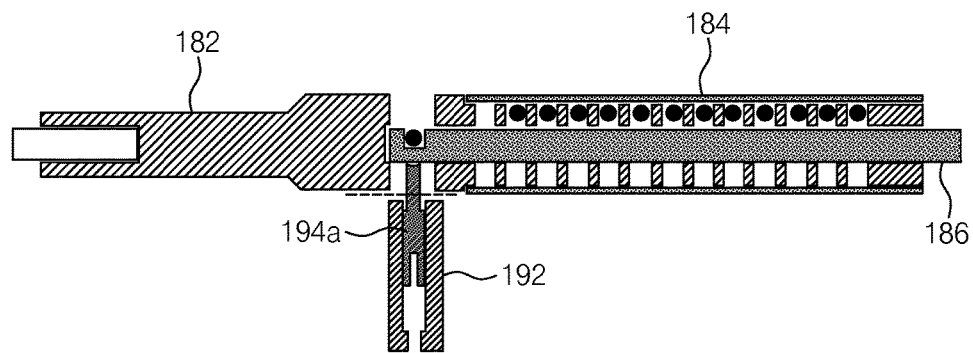
Figure 3N:
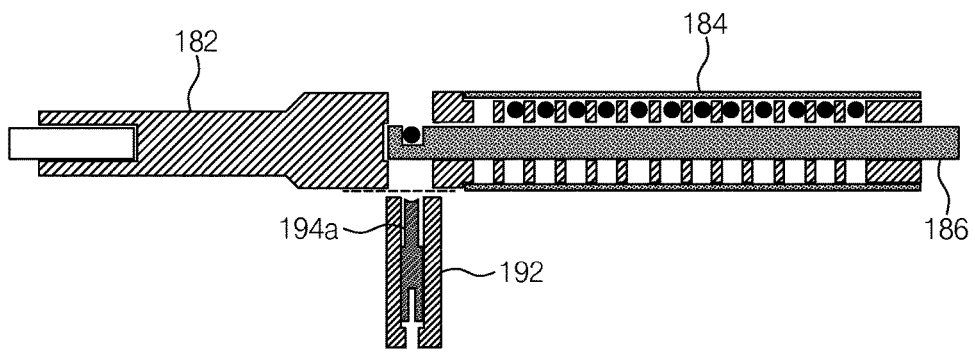
Figure 3O:
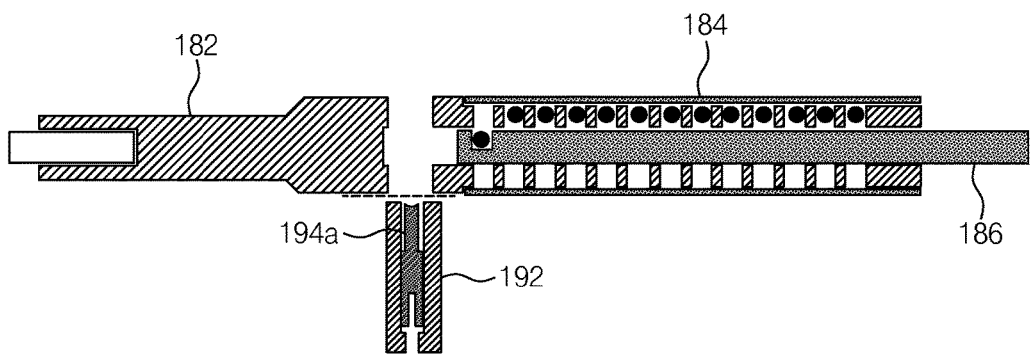
Figure 3P:
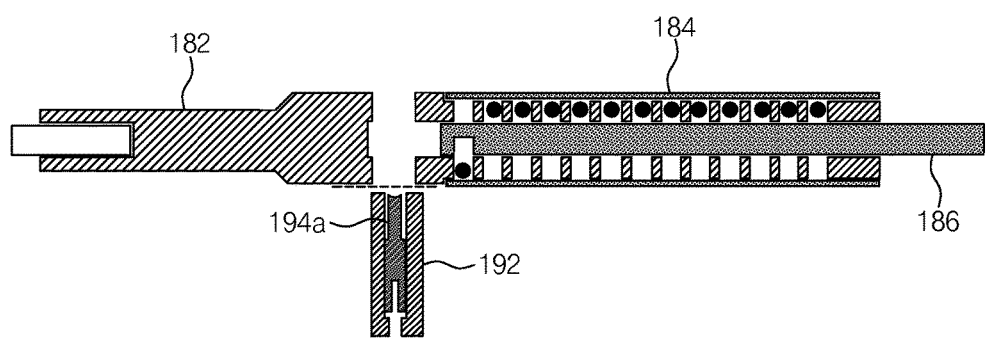
Figure 3Q:
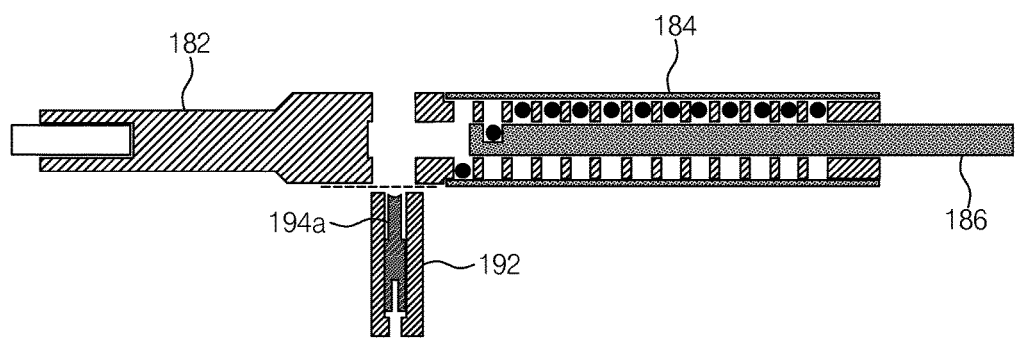

FIGS. 3A to 3Q illustrate an operating method of a sample loading device according to an embodiment of the present disclosure.

Referring to FIG. 3A, a sample loading bar 185 includes sample grooves 185a that are in the form of a cylinder and are formed at first intervals in a lengthwise direction. Samples 12 are mounted in the sample grooves 185a of the sample loading bar 185, respectively.

The sample loading bar 185 is inserted into a loading bar inserting hole 183e of a sample container 180.

Referring to FIG. 3B, the sample container 180 and the sample loading bar 185 are rotated together 180 degrees. Thus, the sample 12 may be all stored on a bottom surface of the sample container 180. In this case, a plane portion 183c of the sample container 180 may be disposed face upward.

Referring to FIG. 3C, the sample loading bar 185 is removed.

Referring to FIG. 3D, a sample transfer bar 186 is inserted into the loading bar inserting hole 183e. The sample transfer bar 186 may be in the form of a cylinder and may have an outer circumferential surface on which a single transfer groove 186*a* is formed. The transfer groove 186*a* may match a position of a first sample. In order for the transfer groove 186*a* to view a sample, the sample transfer bar 186 may be inserted such that the transfer groove 186*a* faces downward. In this case, the plane portion of the sample container 186 may be disposed to face upward. In addition, the sample transfer bar 186 may be connected to a rotary and linear motion part.

Referring to FIG. 3E, the sample container 180 and the sample transfer bar 186 may be rotated 180 degrees. In this case, the plane part 183*c* of the sample container 180 is disposed to face downward and the transfer groove 183*a* may be disposed to face upward. A first sample may be mounted in the transfer groove 186*a*.

Then, a connection part 187 may be inserted into a support groove of the sample container 180 and may be fixed to a vacuum chamber 14.

Then, a vacuum chamber 14 may be exhausted to be maintained at a vacuum state.

Referring to FIG. 3F, the first sample may be disposed on a sample transfer vertical through-hole 183*a* by the sample transfer bar 186.

Referring to FIG. 3G, a loading tip storage part 192 moves and a standard loading tip 194*a* may be aligned with a lower portion of the first sample.

Referring to FIG. 3H, the sample transfer bar 186 may be rotated 180 degrees to drop the sample 12 and the first sample may be mounted on the standard loading tip 194*a*.

Referring to FIG. 3I, the sample transfer bar 185 may move back.

The standard loading tip 194*a* may be disposed between a top electrode and a bottom electrode by a vertical motion of a vertical transfer part 174. Thus, the first sample on the standard loading tip 194 may be electrostatically levitated by a high voltage applied between the top electrode and the bottom electrode. The standard loading tip 194*a* may descend to be stored in the loading tip storage part 192.

Then, the first sample may be fused by a heating laser. When a predetermined test is completed, the first sample may be cooled by radiation. The first sample may be subjected to a crystallization step while being levitated. In order to achieve this, a needle tip having a predetermined crystal structure is selected by moving the loading tip storage part 192. The selected needle tip may come in contact with a bottom surface of the electrostatically levitated sample by the vertical transfer part 174.

Then, the standard loading tip 194*a* may be vertically lifted by the vertical transfer part 174 to be disposed below the first sample. Then, the high voltage applied between the top electrode and the bottom electrode may be removed and the first sample may be mounted on the standard loading tip 194*a*.

Referring to FIG. 3J, the standard loading tip 194 may be descent to locate the first sample at a lower portion of the sample transfer vertical through-hole 183*a*.

Referring to FIG. 3K, a transfer groove 186*a* of the sample transfer bar 186 may be disposed to face an under surface and may be disposed on the sample transfer vertical through-hole 183*a*

Referring to FIG. 3L, the vertical transfer part 174 may locate the first sample disposed on the standard lading tip 194*a* in the transfer groove 186*a* while lifting the standard loading tip 194*a*.

Referring to FIG. 3M, as the sample transfer bar 186 is rotated 180 degrees, the first sample may be mounted in the transfer groove 186*a*.

Referring to FIG. 3N, the standard loading tip 194*a* may be disposed at the loading tip storage part 192.

Referring to FIG. 3O, as the sample transfer bar 186 moves back, the first sample may be disposed on the sample storage vertical through-hole 183*d*.

Referring to FIG. 3P, as the sample transfer bar 186 is rotated 180 degrees, the first sample may be stored at a lower portion of an empty sample storage vertical through-hole 183*d*.

Referring to FIG. 3Q, the sample transfer bar 186 may be rotated 180 degrees and move back to mount a second sample in the transfer groove 186*a*. The foregoing operations may be repeated until completion of the test on all the samples.

High-purity single crystal and single-crystal seed may be used in various tests. The single crystal may be used as a seed for crystal growth. Thus, an electrostatic levitation apparatus according to the present disclosure may be used to form the single crystal. An electrostatically levitated fused liquid sample may exist in a meta-stable state of a supercooling state.

When a needle tip having a predetermined crystal structure comes in contact with a liquid sample, a meta-stable state of the liquid sample may match the crystal structure of the needle tip. In this case, the liquid sample may be crystallized to the crystal structure of the needle tip that cannot be obtained in a normal stable liquid state. In the stable liquid state, the needle tip comes in contact with the stable liquid to form a high-purity single crystal. In addition, when the meta-stable includes a plurality of crystal structures in spite of the same liquid sample, the liquid sample may be crystallized according to the crystal structure of the needle tip.

The liquid sample of a supercooled state may have a microstructure that varies depending on crystallization speed. A dendrite is a crystal where when a fused metal coagulates, metals are regularly accumulated on the basis of a small nucleus. When cooling speed is high, the number of simultaneously occurring branches is large while the number of growing crystal grains is small.

When the needle tip comes in contact with the liquid sample, crystallization speed may vary depending on the supercooling degree of the liquid. Thus, a microstructure of a crystal may be changed. In this regard, material properties depending on the crystallization speed of the sample may be studied.

Figure 4:
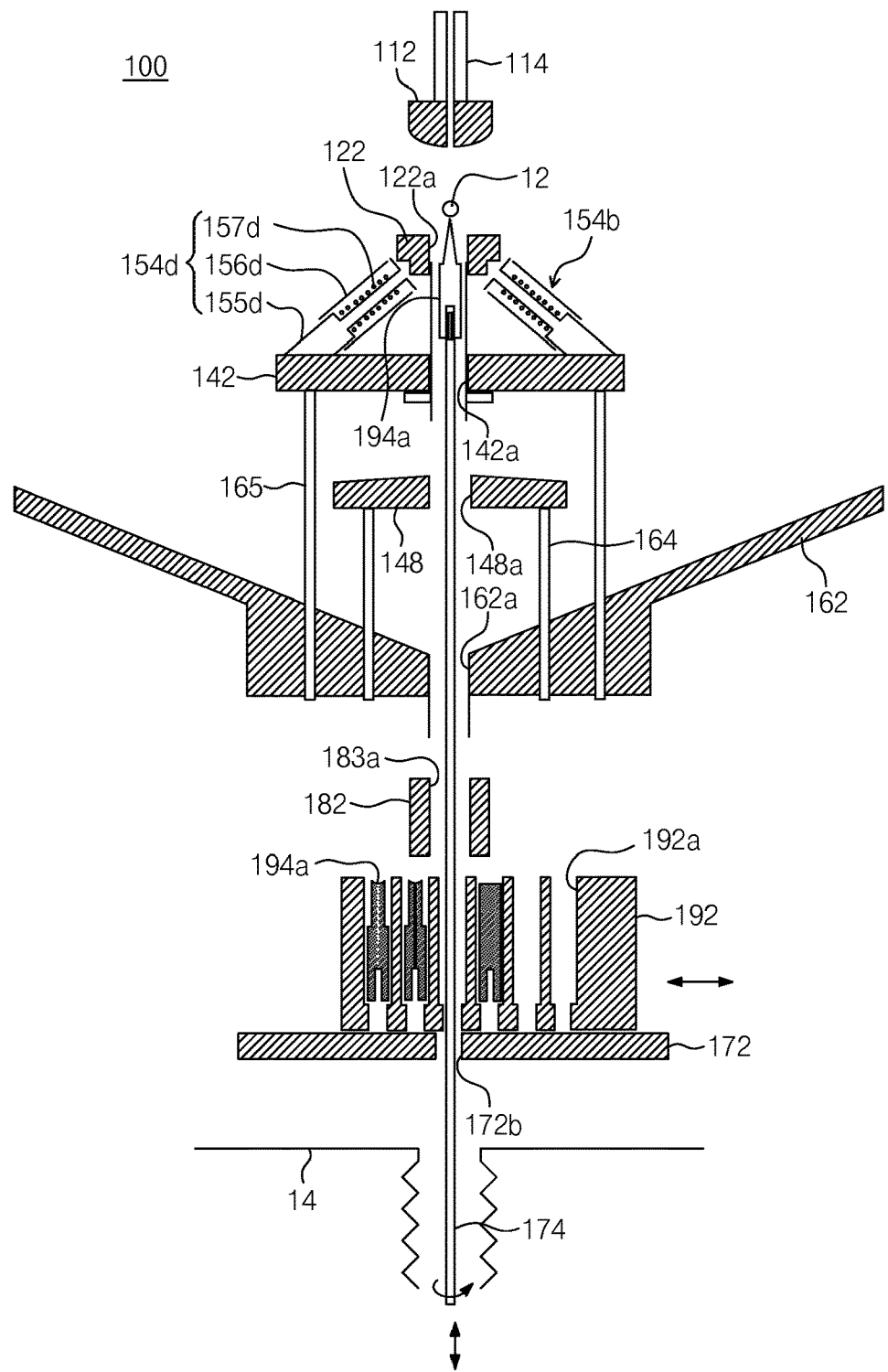
FIG. 4 illustrates an electrostatic levitation apparatus according to another embodiment of the present disclosure.

FIG. 4 illustrates an electrostatic levitation apparatus according to another embodiment of the present disclosure. In FIG. 4, the same components or parts as those shown in FIGS. 1 to 3 are designated with the same numerals and their explanations will be omitted.

Referring to FIG. 4, an electrostatic levitation apparatus may be used as a single crystal growing apparatus. A sample 12 may be disposed between a top electrode 112 and a bottom electrode 122 using a standard loading tip 194*a* having an end-dented groove for transferring the sample 12. The standard loading tip 194 may be ascent to be stored in a loading tip storage part 192.

Then, the loading tip storage part 192 may move along a trench 172*a* to align a needle tip with a dish bottom plate through-hole 172*b*.

Then, an electric field applied between the top electrode 112 and the bottom electrode 122 may electrostatically levitate the sample 12.

Then, a heating laser 23 may heat and fuse the electrostatically levitated sample 12.

Then, when the beam of the heating laser 23 is removed after the sample 12 is fused, the fused liquid sample 12 may exist in a supercooled state that is converted from the electrostatically levitated state by radiation.

Then, the needle tip 194c may be lifted to come in contact with the supercooled fused liquid sample 12. A sharp-needle-type needle tip 194c may induce a predetermined crystal structure which may be generated from the supercooled fused liquid sample 12 of a meta-stable state. Accordingly, the liquid sample 123 may be crystallized through phase transition. Additionally, the needle tip 194c may perform a rotary motion.

For example, when the sample 12 is silicon, a phase of the sample 12 may transit to a single crystal. The needle tip 194c may have a silicon crystal structure. Accordingly, the liquid sample 12 may be crystallized to a solid state. The crystallized sample 12 may be used as a single-crystal seed used in another crystal growing method. If a meta-stable state of the liquid sample 12 of the supercooled state has a plurality of crystal structures, a predetermined one of the crystal structures may be selected according to the crystal structure of the needle tip 194c.

The needle tip 194c may come in contact with the supercooled fused liquid sample 12 to adjust crystallization speed. Thus, a micro-crystal structure of the cooled solid sample may be changed.

After coming in contact with the liquid sample 12, the needle tip 194c is re-descent to be stored in the loading tip storage part 192.

Then, the loading tip storage part 192 may move along a trench to align the standard loading tip 194a with the dish bottom plate through-hole 172b. The standard loading tip 194a may be lifted to collect a levitated sample.

The needle tip 194c may induce a meta-stable crystal phase in a liquid state, induce single-crystal growth, and generate a single-crystal seed. In addition, crystallization speed of the supercooled liquid sample may be controlled according to the supercooling degree and a contact between the supercooled liquid sample and the needle tip 194c. Thus, various microstructures of the crystallized sample may be generated.

Figure 5:
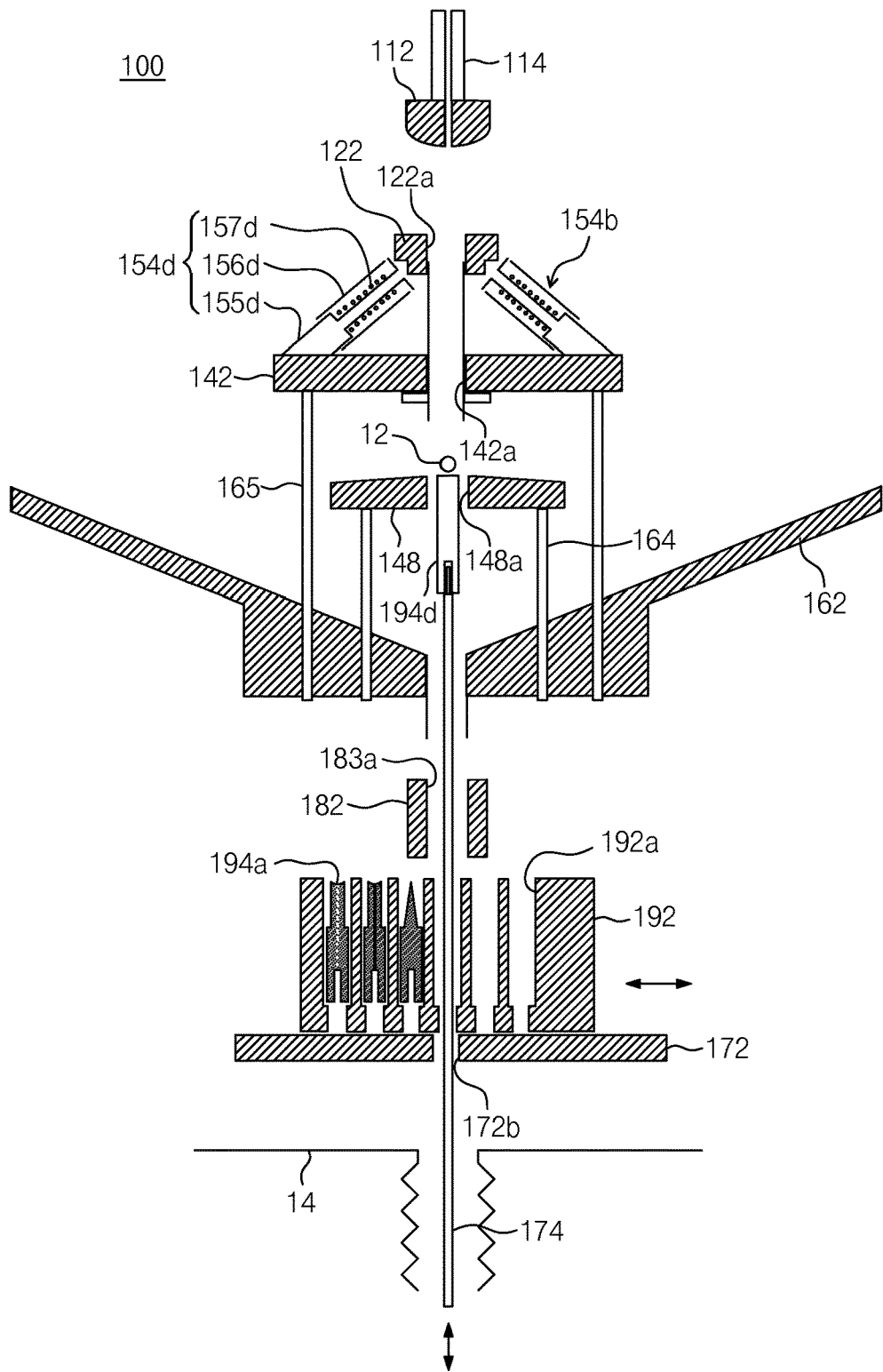
FIG. 5 illustrates an electrostatic levitation apparatus according to another embodiment of the present disclosure.

FIG. 5 illustrates an electrostatic levitation apparatus according to another embodiment of the present disclosure. In FIG. 5, the same components or parts as those shown in FIGS. 1 to 3 are designated with the same numerals and their explanations will be omitted.

Referring to FIG. 5, an electrostatic levitation apparatus 100 may include a quenching plate 148. The quenching plate 148 may be disposed between an electrode support 142 and a collection dish 162. A radiation thermometer 149 may be mounted on a vacuum chamber to check crystallization speed, cooling speed, and temperature.

A sample 12 may be disposed between a top electrode and a bottom electrode using a standard loading tip 194a having an end-dented groove for transferring the sample. The standard loading tip 194a may be descent to be stored in a loading tip storage part 192. Then, the loading tip storage part 192 may move along a trench 192a to align a quenching tip 194d with a dish bottom plate through-hole 172b.

Then, an electric field applied between the top electrode and the bottom electrode may electrostatically levitate the sample.

Then, a heating laser 23 may heat and fuse the electrostatically levitated sample 12.

Then, when the heating laser 23 is removed after the sample 12 is fused, the fused liquid sample 12 may exist in a supercooled state that is converted from the electrostatically levitated state by radiation.

Then, a quenching tip 194d may be lifted to a top surface of the quenching plate 142. When the electric field between the top electrode and the bottom electrode is removed, the supercooled fused liquid sample may fall on the quenching tip 194d to be quickly cooled. The radiation thermometer 149 may measure crystallization speed, cooling speed, and temperature of the sample 12.

As the supercooled liquid sample and the quenching tip 194d come in contact with each other, the supercooled liquid sample may be quickly cooled. Thus, a meta-stable crystal phase may be obtained.

Figure 6:
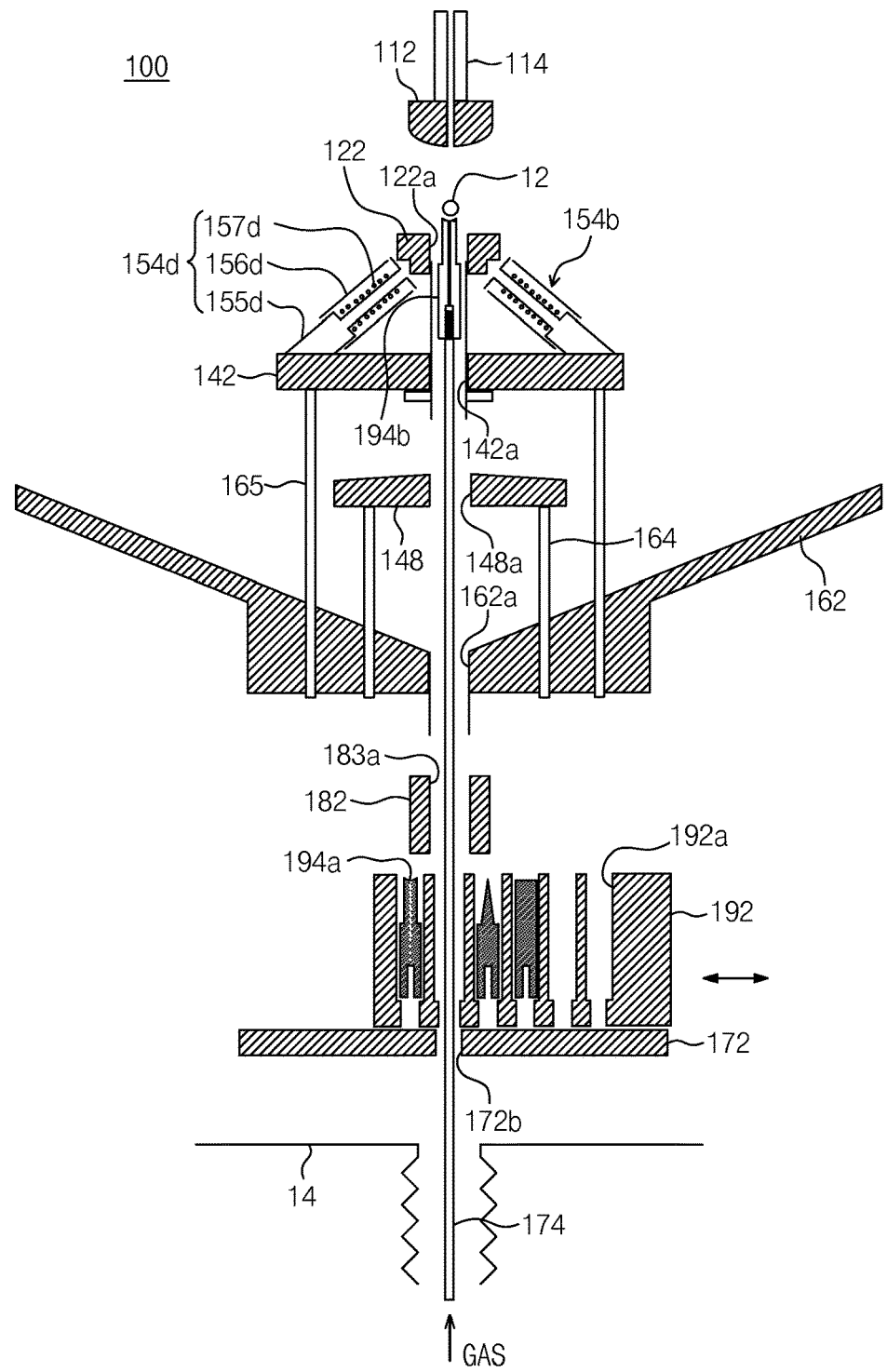
FIG. 6 illustrates an electrostatic levitation apparatus according to another embodiment of the present disclosure.

FIG. 6 illustrates an electrostatic levitation apparatus according to another embodiment of the present disclosure. In FIG. 6, the same components or parts as those shown in FIGS. 1 to 3 are designated with the same numerals and their explanations will be omitted.

Referring to FIG. 6, a sample 12 may be disposed between a top electrode and a bottom electrode using a gas levitation loading tip 194b for transferring the sample 12. The gas levitation loading tip 194b may include a nozzle disposed in its center and receive a gas via the nozzle. Thus, the sample 12 may be levitated.

Then, a heating laser 23 may heat and fuse the electrostatically levitated sample 12.

Then, when the heating laser 23 is removed after the sample 12 is fused, the fused liquid sample 12 may exist in a supercooled state that is converted from the electrostatically levitated state by radiation.

According to a modified embodiment of the present disclosure, a sample 12 may be electrostatically levitated using a standard loading tip 194 and a gas levitation loading tip 194b may be used to provide a predetermined gas to the sample 12. In this case, a surface of the sample 123 may be coated with a new material.

According to a gas levitation method according to a modified embodiment of the present disclosure, a top electrode and a bottom electrode for use in electrostatic levitation may be removed. However, when an auxiliary electrode is a conductive sample, the top electrode and the bottom electrode may be used to perform a rotary motion.

As described above, a sample loading device according to an embodiment of the present disclosure may successively samples to a standard loading tip and a test tip may come in contact with an electrostatically levitated sample to provide various tests.

A needle tip may induce a meta-stable crystal phase in a supercooled liquid state and achieve growth of a single crystal and generation of single-crystal seeds. The needle tip may control crystallization speed according to contact between a liquid sample and the needle tip depending on the supercooling degree to adjust a microstructure.

After dropping the supercooled liquid on a flat tip, a quick cooling tip may quickly cool the supercooled liquid to provide a meta-stable crystal phase. After dropping a formed solid phase on the flat tip, the quick cooling tip may quickly cool the solid phase. A gas levitation loading tip may levitate a sample with a gas.

According to an embodiment of the present disclosure, various tips may be provided to perform various tests according to test purposes.

According to an embodiment of the present disclosure, a size of a vacuum chamber decreases as a size of a cartridge for loading a sample decreases. Thus, vacuum may be achieved within shorter time to reduce time required for a test. Moreover, after a test is performed, the sample may be collected to an original cartridge. Thus, loss of the sample may be prevented using a collection dish having a funnel structure.

In an electrostatic levitation apparatus according to an embodiment of the present disclosure, a test tip may come in contact with an electrostatically levitated sample to provide various tests. Thus, new properties may be induced from a supercooled liquid sample. In addition, an ultrapure single crystal and a single-crystal seed may be grown.

A needle tip may induce a meta-stable crystal phase in a supercooled liquid state and achieve growth of a single crystal and generation of a single-crystal seed. The needle tip may control crystallization speed according to contact between a liquid sample and the needle tip depending on the supercooling degree to adjust a microstructure.

After dropping the supercooled liquid on a flat tip, a quick cooling tip may quickly cool the supercooled liquid to provide a meta-stable crystal phase. After dropping a formed solid phase on the flat tip, the quick cooling tip may quickly cool the solid phase. A gas levitation loading tip may levitate a sample with a gas.

According to an embodiment of the present disclosure, various tips may be provided to perform various tests under a single environment.

According to an embodiment of the present disclosure, a size of a vacuum chamber decreases as a size of a cartridge for loading a sample decreases. Thus, vacuum may be achieved within shorter time to reduce time required for a test. Moreover, after a test is performed, the sample may be collected to an original cartridge. Thus, loss of the sample may be prevented using a collection dish having a funnel structure.

Although the present disclosure has been described in connection with the embodiment of the present disclosure illustrated in the accompanying drawings, it is not limited thereto. It will be apparent to those skilled in the art that various substitutions, modifications and changes may be made without departing from the scope and spirit of the present disclosure.

What is claimed is:

1. A sample loading device comprising:
a sample storage part including a cylindrical sample standby part having an external diameter of a first diameter and a cylindrical sample loading part having an external diameter of a second diameter; and
a cylindrical sample cover part having an external diameter of the second diameter and covering the sample standby part,
wherein the sample storage part has a loading bar inserting hole that is formed in its center in a lengthwise direction,
the loading bar inserting hole is formed through the sample standby part and is formed successively through a portion of the sample loading part,
the sample standby part has sample storage vertical through-holes that are formed at regular first intervals in a lengthwise direction and penetrate in a direction perpendicular to the lengthwise direction,
the sample loading part has a single sample transfer vertical through-hole, and
the sample transfer vertical through-hole is formed on a surface where the sample storage vertical through-hole is viewed, penetrates the sample loading part, and is connected to the loading bar inserting hole.

2. The sample loading device as set forth in claim 1, wherein one surface to which the sample transfer vertical through-hole is exposed is formed as a plane.

3. The sample loading device as set forth in claim 1, further comprising:
a slit formed on both side surface of the sample loading part to be perpendicular to a direction in which the sample transfer vertical through-hole is formed,
wherein the slit is connected to the sample transfer vertical through-hole.

4. The sample loading device as set forth in claim 1, further comprising:
a cylindrical sample loading bar that has sample grooves formed at the first intervals in the lengthwise direction and is inserted into the loading bar inserting hole,
wherein a sample is mounted in the sample grooves.

5. The sample loading device as set forth in claim 1, further comprising:
a cylindrical sample transfer bar that has a single transfer groove formed on its outer circumferential surface and is inserted into the loading bar inserting hole,
wherein a sample is mounted in the transfer groove to be transferred.

6. The sample loading device as set forth in claim 5, wherein the sample transfer bar locates the sample mounted in the transfer groove in the sample transfer vertical through-hole,
which further comprises a loading tip storage part adapted to store a standard loading tip, the loading tip storage part being disposed below the sample transfer vertical through-hole and having an end-dented groove for transferring the sample,
wherein the sample is mounted in the standard loading tip via the sample transfer vertical through-hole, and
the standard loading tip is vertically lifted to be disposed between a top electrode and a bottom electrode for electrostatically levitating the sample.

7. The sample loading device as set forth in claim 6, wherein the loading tip storage part comprises: a plurality of tip storage through-holes aligned in a line; and a test tip that is mounted in the tip storage through-holes and has a different structure from the standard loading tip.

8. The sample loading device as set forth in claim 7, wherein the test tip comprises at least one of a needle-shaped needle tip for inducing a meta-stable crystal phase generated from a supercooled liquid fused liquid sample, a gas levitation loading tip that includes a nozzle disposed in its center for discharging a gas to levitate the sample and has an end-dented groove, and a quick cooling tip having a flat end.

9. The sample loading device as set forth in claim 1, further comprising at least one of:
a top electrode;
a bottom electrode disposed to be spaced apart from the top electrode, the bottom electrode having a bottom electrode through-hole formed in its center;
first to fourth auxiliary electrodes symmetrically disposed on a plane perpendicular to an axis connecting a center of the top electrode and the center of the bottom electrode to each other;
a cylindrical bottom electrode support connected to the bottom electrode through-hole of the bottom electrode and made of a dielectric material;
an electrode support plate on which the bottom electrode support is mounted and an auxiliary electrode support rod for supporting the auxiliary electrodes is mounted, the electrode support plate having an electrode support plate through-hole in its center;
a conic collection dish disposed below the electrode support plate, the collection dish having a collection dish through-hole formed in its center;

an electrode support plate support rod adapted to connect the collection dish and the electrode support plate to each other;
a quenching plate disposed between the collection dish and the electrode support plate, the quenching plate having a quenching plate through-hole formed in its center;
a quenching plate support rod adapted to connect the quenching plate and the collection dish to each other;
a sample container support mounted on a bottom surface of the collection dish, the sample container support having a sample container through-hole formed in a horizontal direction;
a dish bottom plate disposed below the sample cover part, the dish bottom plate having a trench extending in a direction perpendicular to a direction in which the sample cover part extends; and
a loading tip storage part inserted into the trench and disposed between the dish bottom plate and a sample container, the loading tip storage part having a through-hole formed in its center.

10. The sample loading device as set forth in claim 1, wherein the sample storage part further comprises a sample container support successively connected to the sample standby part,
the sample container support has one end where a support groove formed in a center of a sample container in an extending direction of the end and is fixed to a vacuum chamber via the support groove.

11. A sample loading device comprising:
a rod-shaped sample standby part;
a sample storage part successively connected in an extending direction of the sample standby part, the sample storage part including a sample loading part; and
a sample cover part to cover the sample standby part,
wherein the sample storage part has a loading bar inserting hole formed in its center in a lengthwise direction,
the loading bar inserting hole is formed through the sample standby part and is formed successively through a portion of the sample loading part,
the sample standby part has vertical through-holes that have regular first intervals in a lengthwise direction and penetrate in a direction perpendicular to the lengthwise direction,
the sample loading part has a single sample transfer vertical through-hole, and
the sample transfer vertical through-hole is formed on a surface where the sample storage vertical through-hole is viewed, penetrates the sample loading part, and is connected to the loading bar inserting hole.

* * * * *